(12) United States Patent
Loetscher et al.

(10) Patent No.: US 7,029,862 B1
(45) Date of Patent: Apr. 18, 2006

(54) METHOD FOR IDENTIFYING LIGANDS, INHIBITORS OR PROMOTERS OF CXC CHEMOKINE RECEPTOR 3

(75) Inventors: Marcel Loetscher, Koeniz (CH); Bernhard Moser, Stettlen (CH)

(73) Assignee: Theodor-Kocher Institute, Bern (CH)

( * ) Notice: Subject to any disclaimer, the term of this patent is extended or adjusted under 35 U.S.C. 154(b) by 0 days.

(21) Appl. No.: 09/633,541

(22) Filed: Aug. 7, 2000

Related U.S. Application Data

(63) Continuation of application No. 08/709,838, filed on Sep. 10, 1996, now Pat. No. 6,140,064.

(51) Int. Cl.
*G01N 33/53* (2006.01)
(52) U.S. Cl. .................. 435/7.2; 435/7.1; 435/325; 530/350; 530/351; 530/387.9
(58) Field of Classification Search ............... 435/7.1, 435/7.2, 325; 530/350, 351, 387.9
See application file for complete search history.

(56) References Cited

U.S. PATENT DOCUMENTS

| | | | |
|---|---|---|---|
| 5,543,503 A | 8/1996 | Chuntharapai et al. | 530/388.22 |
| 5,629,283 A | 5/1997 | Nicola et al. | 514/2 |
| 6,140,064 A | 10/2000 | Loetscher et al. | |
| 6,184,358 B1 | 2/2001 | Loetscher et al. | |
| 2005/0112119 A1 | 5/2005 | Qin et al. | |

FOREIGN PATENT DOCUMENTS

| | | |
|---|---|---|
| DE | 43 32 256 C1 | 3/1995 |
| WO | WO 91/02063 | 2/1991 |
| WO | WO 94/12635 | 6/1994 |
| WO | WO 94/24282 | 10/1994 |
| WO | WO 95/08576 | 3/1995 |
| WO | WO 97/25340 | 7/1997 |

OTHER PUBLICATIONS

Mikayama T. Molecular cloning and functional expression of a cDNA encoding glycosylation-inhibiting factor. Proc. Natl. Acad. Sci. USA vol. 90, pp. 10056-10060, 1993.*
Voet et al. Biochemistry. 1990. John Wiley & Sons, Inc.. pp. 126-128 and 228-234.*
Voet et al. Biochemistry. 1990. John Wiley & Sons, Inc. 126-128 and 228-234.*
Mickle JE et al. Genotype-phenotype relationships in cystic fibrosis. Med Clin North Am. May 2000;84(3):597-607.*
Yan et al., Two-amino acid molecular switch in an epithelial morphogen that regulates binding to two distinct receptors. Science 290: 523-527, 2000.*
Murphy, P.M., "The Molecular Biology of Leukocyte Chemoattractant Receptors," *Annu. Rev. Immunol.*, 12:593-633 (1994).
Marchese, A. et al., "Cloning and Chromosomal Mapping of Three Novel Genes, GPR9, GPR10, and GPR14, Encoding Receptors Related to Interleukin 8, Neuropeptide Y, and Somatostatin Receptors," *Genomics*, 29:335-344 (1995).
Gen Bank Accession No. U32674, submitted by Marchese, A. et al., first released Oct. 2, 1995 according to personnel at the National Center for Biotechnology Information.
Taub, D.D., et al., "Recombinant Human Interferon-inducible Protein 10 is a Chemoattractant for Human Monocytes and T Lymphocytes and Promotes T Cell Adhesion to Endothelial Cells," *J. Exp. Med.*, 177:1809-1814.
Sarris, A.H., et al., "Human Interferon-inducible Protein 10: Expression and Purification of Recombinant Protein Demonstrate Inhibition of Early Human Hematopoietic Progenitors," *J. Exp. Med.*, 178:1127-1132 (1993).
Luster, A.D. and Leder, P., "IP-10, a -C-X-C- Chemokine, Elicits a Potent Thymus-dependent Antitumor Response In Vivo," *J. Exp. Med.*, 176:1057-1065 (1993).
Angiolillo, A.L., et al., "Human Interferon-inducible Protein 10 is a Potent Inhibitor of Angiogenesis In Vivo," *J. Exp. Med.*, 182:155-162 (1995).

(Continued)

*Primary Examiner*—Joseph Murphy
*Assistant Examiner*—Gregory S. Emch
(74) *Attorney, Agent, or Firm*—Hamilton, Brook, Smith & Reynolds, P.C.

(57) ABSTRACT

The invention relates to methods of identifying ligands, and inhibitors (e.g., antagonists) or promoters (e.g., agonists) of receptor function, including methods in which host cells comprising a nucleic acid encoding a CXCR3 or variant thereof are used in an assay to identify and assess the efficacy of ligands, inhibitors or promoters. Inhibitors and promoters of receptor function can be used to modulate receptor activity, permitting selective inhibition of lymphocyte function, particularly of effector cells such as activated T lymphocytes and NK cells for therapeutic purposes.

62 Claims, 4 Drawing Sheets

OTHER PUBLICATIONS

Luster, A.D., et al., "The IP-10 Chemokine Binds to a Specific Cell Surface Heparan Sulfate Site Shared with Platelet Factor 4 and Inhibits Endothelial Cell Proliferation," *J. Exp. Med.,* 182:219-231 (1995).

Taub, D.D., et al., "α and β Chemokines Induce NK Cell Migration and Enhance NK-Mediated Cytolysis," *J. Immunol.,* 155:3877-3888 (1995).

Luster, A.D., et al., "γ-Interferon Transcriptionally Regulates an Early-Response Gene Containing Homology to Platelet Proteins," *Nature,* 315:672-676 (1985).

Farber, J.M., "A Macrophage mRNA Selectively Induced by γ-Interferon Encodes a Member of the Platelet Factor 4 Family of Cytokines," *Proc. Natl. Acad. Sci. USA,* 87:5238-5242 (1990).

Farber, J.M., "HuMIG: A New Human Member of the Chemokine Family of Cytokines," *Biochem. Biophys. Res. Commun.,* 192(1):223-230 (1993).

Liao, F., et al., "Human Mig Chemokine: Biochemical and Functional Characterization," *J. Exp. Med.* 182:1301-1314 (1995).

Föster, R., et al., "A General Method for Screening mAbs Specific for G-protein Coupled Receptors as Exemplified by Using Epitope Tagged BLR1-Transfected 293 Cells and Solid-Phase Cell ELISA," *Biochem. Biophys. Res. Commun.,* 196(3):1496-1503 (1993).

Miller, M.S. and Krangel, M.S., "Biology and Biochemistry of the Chemokines: A Family of Chemotactic and Inflammatory Cytokines," *Critical Reviews in Immunology,* 12(1, 2):17-46 (1992).

Gayle III, R.B., et al., "Importance of the Amino Terminus of the Interleukin-8 Receptor in Ligand Interactions," *J. Biol. Chem.,* 268(10):7283-7289 (1993).

Sprenger, H., et al., "Structure, Genomic Organization and Expression of the Human Interleukin-8 Receptor B Gene," *J. Biol. Chem.,* 269(15):11065-11072 (1994).

Oliveira, L., et al., "A Common Motif in G-Protein-Coupled Seven Transmembrane Helix Receptors," *J. Computer-Aided Molecular Design,* 7:649-658 (1993).

Dewald, B., et al., "IP-10, a γ-interferon-inducible Protein Related to Interleukin-8, Lacks Neutrophil Activating Properties," *Immunol. Let.,* 32:81-84 (1992).

Loetscher, M., et al., "Chemokine Receptor Specific for IP10 and Mig: Structure, Function, and Expression in Activated T-Lymphocytes," *J. Exp. Med.,* 184:963-969 (1996).

Kaplan, G., et al., "The Expression of a γ Interferon-induced Protein (IP-10) in Delayed Immune Responses in Human Skin," *J. Exp. Med.,* 166:1098-1108 (1987).

Gottlieb, A.B., et al., "Detection of a γ Interferon-induced Protein IP-10 in Psoriatic Plaques," *J. Exp. Med.,* 168:941-948 (1988).

George, D.G., et al., "Current Methods in Sequence Comparison and Analysis," *Macromolecular Sequencing and Synthesis Selected Methods and Applications,* (Alan R. Liss, Inc.) pp. 127-149 (1988).

Cunningham, B.C., and Wells, J.A., "High-Resolution Epitope Mapping of hGH-Receptor Interactions by Alaine-Scanning Mutagenesis," *Science,* 244:1081-1085 (1989).

Strieter, Robert M., et al., "CXC Chemokines in Angiogenesis of Cancer," *Seminars in Cancer Biology,* 14:195-200, (2004).

Miller, G., "Breaking Down Barriers," *Science,* 297:1116-1118 (2002).

Murphy, P.M., "The Molecular Biology of Leukocyte Chemoattractant Receptors." *Annu. Rev. Immunol.,*12:593-633 (1994).

Marchese, A. et al., "Cloning and Chromodomal Mapping of Three Novel Genes, GPR9, GPR10, and GPR14. Encoding Receptors Related to Interleukin 8, Neuropeptide Y, and Somatostatin Receptors," *Genomics,*29:335-344 (1995).

Gen Bank Accession No. U32674, submitted by Marchese, A. et al., first released Oct. 2, 1995 according to personnel at the National Center for Biotechnology Information.

Taub, D.D., et al., "Recombinant Human Interferon-inducible Protein 10 is a Chemoattractant for Human Monocytes and T Lymphocytes and Promotes T Cell Adhesion to Endorhelial Cells,"*J. Exp. Med.,*177:1809-1814 (1993).

Sarris, A.H., et al., "Human Interferon-inducible Protein 10: Expression and Purification of Recombinant Protein Demonstrate Inhibition of Early Human Hematopoietic Progenitors," *J. Exp. Med.,*178:1127-1132 (1993).

Luster, A.D. and Leder, P., "IP-10, a -C-X-C- Chemokine, Elicits a Potent Thymus-dependent Antitumor Response In Vivo," *J. Exp. Med.,*178:1057-1065 (1993).

Angiolillo. A.L., et al., "Human Interferon-inducible Protein 10 is a Potent Inhibitor of Angiogenesis In Vivo," *J. Exp. Med.,*182:155-162 (1995).

Luster, A.D., et al., "The IP-10 Chemokine Binds to Specific Cell Surface Heparan Sulfate Site Shared with Platelet Factor 4 and Inhibits Endothelial Cell Proliferation, "*J. Exp. Med.,* 182:219-231 (1995).

Taub. D.D., et al., "α and β Chemokines Induce NK Cell Migration and Enhance NK-Medicated Cytolysis," *J. Immunol.,*155:3877-3888 (1995).

Luster, A.D., et al., "γ-Interferon Transcriptionally Regulates an Early-Response Gene Containing Homology to Plateler Proteins, " *Nature,* 315:672-676 (1985).

Farber, J.M., "A Macrophage mRNA Selectively Induced by γ-Interferon Encodes a Member of the Plateler Factor 4 Family of Cytokines, " *Proc. Natl. Acad. Sci. USA,*87:5238-5242 (1990).

Farber, J.M., "HuMig: A New Human Member of the Chemokine Family of Characterization," *J. Exp. Med.*182:1301-1314 (1995).

Liao, F., et al., "A General Method for Screening mAbs Specific for G-protein Coupled Receptors as Exemplified by Using Epitope Tagged BLR1-Transfected 293 Cells and Solid-Phase Cell ELISA," *Biochem. Biophys. Res. Commun.,*196 (3) :1496-1503 (1993).

Forster, P., et al., "Human Mig Chemokine: Biochemical and Functional Characterization," *J. Exp. Med.*182:1301-1314 (1995).

Miller, M.D. and Krangel, M.S., "Biology and Biochemistry of the Chemokines: A Family of Chemotactic and Inflammatory Cytokines," *Critical Reviews in Immunology,*12(1,2) :17-46 (1992).

Gayle III, R.B., et al., "Importance of the Amino Terminus of the Interleukin-8 Receptor in Ligand Interactions," *J. Biol. Chem.,* 269(10) :7283-7289 (1993).

Sprenger, H., et al., "Structure, Genomic Organization, and Expression of the Human Interleukin-8 Receptor B Gene," *J. Biol. Chem.,*269 (15) :11065-11072 (1994).

Oliveira, L., et al., "A Common Motif in G-Protein-Coupled Seven Transmembrane Helix Receptors," *J. Computer-Aided Molecular Design,*7 :649-658 (1993).

Dewald, B., et al., "IP-10, a γ-interferon-inducible Protein Related to Interleukin-8, Lacks Neutrophil Activating Properties," *Immunol. Let.,*32:81-84 (1992).

Loetscher, M., et al., "Chemokine Receptor Specific for IP10 and Mig: Structure, Function, and Expression in Activated T-Lymphocytes," *J. Exp. Med.,* 184:963-969 (1995).

Kaplan, G., et al., "The Expression of a γ Interferon-induced Protein (IP-10) in Delayed Immune Responses in Human Skin," *J. Exp. Med.,* 166:1098-1108 (1987).

Gottlieb, A.B., et al., "Detection of a γ Interferon-induced Protein IP-10 in Psoriatic Plaques," *J. Exp. Med.,* 168:941-948 (1988).

George, D.G., et al., "Current Methods in Sequence Comparison and Analysis," *Macromolecular Sequencing and Synthesis Selected Methods and Applications,* (Alan R. Liss, Inc.) pp. 127-149 (1988).

Cunningham, B.C., and wells, J.A., "High-Resolution Epitope Mapping of hGH-Receptor Interactions by Alanine-Scanning Mutagenesis," *Science,* 244:1081-1085 (1989).

* cited by examiner

```
CCAACCACAA GCACCAAAGC AGAGGGGCAG GCAGCACACC ACCCAGCAGC CAGAGCACCA    60
GCCCAGCCAT GGTCCTTGAG GTGAGTGACC ACCAAGTGCT AAATGACGCC GAGGTTGCCG   120
CCCTCCTGGA GAACTTCAGC TCTTCCTATG ACTATGGAGA AAACGAGAGT GACTCGTGCT   180
GTACCTCCCC GCCCTGCCCA CAGGACTTCA GCCTGAACTT CGACCGGGCC TTCCTGCCAG   240
CCCTCTACAG CCTCCTCTTT CTGCTGGGGC TGCTGGGCAA CGGCGCGGTG GCAGCCGTGC   300
TGCTGAGCCG GCGGACAGCC CTGAGCAGCA CCGACACCTT CCTGCTCCAC CTAGCTGTAG   360
CAGACACGCT GCTGGTGCTG ACACTGCCGC TCTGGGCAGT GGACGCTGCC GTCCAGTGGG   420
TCTTTGGCTC TGGCCTCTGC AAAGTGGCAG GTGCCCTCTT CAACATCAAC TTCTACGCAG   480
GAGCCCTCCT GCTGGCCTGC ATCAGCTTTG ACCGCTACCT GAACATAGTT CATGCCACCC   540
AGCTCTACCG CCGGGGGCCC CCGGCCCGCG TGACCCTCAC CTGCCTGGCT GTCTGGGGGC   600
TCTGCCTGCT TTTCGCCCTC CCAGACTTCA TCTTCCTGTC GGCCCACCAC GACGAGCGCC   660
TCAACGCCAC CCACTGCCAA TACAACTTCC CACAGGTGGG CCGCACGGCT CTGCGGGTGC   720
TGCAGCTGGT GGCTGGCTTT CTGCTGCCCC TGCTGGTCAT GGCCTACTGC TATGCCCACA   780
TCCTGGCCGT GCTGCTGGTT TCCAGGGGCC AGCGGCGCCT GCGGGCCATG CGGCTGGTGG   840
TGGTGGTCGT GGTGGCCTTT GCCCTCTGCT GGACCCCCTA TCACCTGGTG GTGCTGGTGG   900
ACATCCTCAT GGACCTGGGC GCTTTGGCCC GCAACTGTGG CCGAGAAAGC AGGGTAGACG   960
TGGCCAAGTC GGTCACCTCA GGCCTGGGCT ACATGCACTG CTGCCTCAAC CCGCTGCTCT  1020
ATGCCTTTGT AGGGGTCAAG TTCCGGGAGC GGATGTGGAT GCTGCTCTTG CGCCTGGGCT  1080
GCCCCAACCA GAGAGGGCTC CAGAGGCAGC ATCGTCTTC CCGCCGGGAT TCATCCTGGT  1140
CTGAGACCTC AGAGGCCTCC TACTCGGGCT TGTGAGGCCG GAATCCGGGC TCCCCTTTCG  1200
CCCACAGTCT GACTTCCCCG CATTCCAGGC TCCTCCCTCC CTCTGCCGGC TCTGGCTCTC  1260
CCCAATATCC TCGCTCCCGG GACTCACTGG CAGCCCCAGC ACCACCAGGT CTCCCGGGAA  1320
GCCACCCTCC CAGCTCTGAG GACTGCACCA TTGCTGCTCC TTAGCTGCCA AGCCCCATCC  1380
TGCCGCCCGA GGTGGCTGCC TGGAGCCCCA CTGCCCTTCT CATTTGGAAA CTAAAACTTC  1440
ATCTTCCCCA AGTGCGGGGA GTACAAGGCA TGGCGTAGAG GGTGCTGCCC CATGAAGCCA  1500
CAGCCCAGGC CTCCAGCTCA GCAGTGACTG TGGCCATGGT CCCCAAGACC TCTATATTTG  1560
CTCTTTTATT TTTATGTCTA AAATCCTGCT TAAAACTTTT CAATAAACAA GATCGTCAGG  1620
ACCTTTTTTT TTTTTTTTTT TTTTTTTTTT TTTTTTTTTT TTTTTTTTT              1670
```

FIG. 1

MVLEVSDHQVLNDAEVAALLENFSSSYDYGENESDSCCTSPPCPQDFSLNFDRAFLPALYSLLFLLGLLGNGAVAAVLLSRRTALSSTDT  90

TM1

FLLHLAVADTLLVLTLPLWAV-DAAVQWVFGSGLCKVAGALFNINFYAGALLLACISFDRYLNIVHATQLYRRGPPARVTLTCLAVWGLC  179

TM2                                TM3                                       TM4

LLFALPDFIFLSAHHDERLNATHCQYNFPQVG------RTALRVIQLVAGFLLPLLVMAYCYAHILAVLLIVSRGQRRL-RAMRLVVVVVV  262

TM4                                             TM5                              TM6

AFALCWTPYHLVLIVDILMDLGALARNCGRESRVDVAKSVTSGLGYMIICCLNPLLYAFVGVKFERMWMLLLR---LGCPNQRGLQRQPS  349

TM7

SSRRDSSWSETSEASYSGL  368

FIG. 2

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 1670 base pairs
        (B) TYPE: nucleic acid
        (C) STRANDEDNESS: double
        (D) TOPOLOGY: unknown (ix) FEATURE:
        (A) NAME/KEY: CDS
        (B) LOCATION: 69..1172

(xi) SEQUENCE DESCRIPTION: SEQ ID NO:1:

```
CCAACCACAA GCACCAAAGC AGAGGGGCAG GCAGCACACC ACCCAGCAGC CAGAGCACCA         60

GCCCAGCC ATG GTC CTT GAG GTG AGT GAC CAC CAA GTG CTA AAT GAC GCC        110
         Met Val Leu Glu Val Ser Asp His Gln Val Leu Asn Asp Ala
           1               5                  10

GAG GTT GCC GCC CTC CTG GAG AAC TTC AGC TCT TCC TAT GAC TAT GGA         158
Glu Val Ala Ala Leu Leu Glu Asn Phe Ser Ser Ser Tyr Asp Tyr Gly
```

-continued

```
        15                  20                  25                  30
GAA AAC GAG AGT GAC TCG TGC TGT ACC TCC CCG CCC TGC CCA CAG GAC        206
Glu Asn Glu Ser Asp Ser Cys Cys Thr Ser Pro Pro Cys Pro Gln Asp
                    35                  40                  45

TTC AGC CTG AAC TTC GAC CGG GCC TTC CTG CCA GCC CTC TAC AGC CTC        254
Phe Ser Leu Asn Phe Asp Arg Ala Phe Leu Pro Ala Leu Tyr Ser Leu
                50                  55                  60

CTC TTT CTG CTG GGG CTG CTG GGC AAC GGC GCG GTG GCA GCC GTG CTG        302
Leu Phe Leu Leu Gly Leu Leu Gly Asn Gly Ala Val Ala Ala Val Leu
            65                  70                  75

CTG AGC CGG CGG ACA GCC CTG AGC AGC ACC GAC ACC TTC CTG CTC CAC        350
Leu Ser Arg Arg Thr Ala Leu Ser Ser Thr Asp Thr Phe Leu Leu His
        80                  85                  90

CTA GCT GTA GCA GAC ACG CTG CTG GTG CTG ACA CTG CCG CTC TGG GCA        398
Leu Ala Val Ala Asp Thr Leu Leu Val Leu Thr Leu Pro Leu Trp Ala
95                  100                 105                 110

GTG GAC GCT GCC GTC CAG TGG GTC TTT GGC TCT GGC CTC TGC AAA GTG        446
Val Asp Ala Ala Val Gln Trp Val Phe Gly Ser Gly Leu Cys Lys Val
                115                 120                 125

GCA GGT GCC CTC TTC AAC ATC AAC TTC TAC GCA GGA GCC CTC CTG CTG        494
Ala Gly Ala Leu Phe Asn Ile Asn Phe Tyr Ala Gly Ala Leu Leu Leu
            130                 135                 140

GCC TGC ATC AGC TTT GAC CGC TAC CTG AAC ATA GTT CAT GCC ACC CAG        542
Ala Cys Ile Ser Phe Asp Arg Tyr Leu Asn Ile Val His Ala Thr Gln
        145                 150                 155

CTC TAC CGC CGG GGG CCC CCG GCC CGC GTG ACC CTC ACC TGC CTG GCT        590
Leu Tyr Arg Arg Gly Pro Pro Ala Arg Val Thr Leu Thr Cys Leu Ala
    160                 165                 170

GTC TGG GGG CTC TGC CTG CTT TTC GCC CTC CCA GAC TTC ATC TTC CTG        638
Val Trp Gly Leu Cys Leu Leu Phe Ala Leu Pro Asp Phe Ile Phe Leu
175                 180                 185                 190

TCG GCC CAC CAC GAC GAG CGC CTC AAC GCC ACC CAC TGC CAA TAC AAC        686
Ser Ala His His Asp Glu Arg Leu Asn Ala Thr His Cys Gln Tyr Asn
                195                 200                 205

TTC CCA CAG GTG GGC CGC ACG GCT CTG CGG GTG CTG CAG CTG GTG GCT        734
Phe Pro Gln Val Gly Arg Thr Ala Leu Arg Val Leu Gln Leu Val Ala
            210                 215                 220

GGC TTT CTG CTG CCC CTG CTG GTC ATG GCC TAC TGC TAT GCC CAC ATC        782
Gly Phe Leu Leu Pro Leu Leu Val Met Ala Tyr Cys Tyr Ala His Ile
        225                 230                 235

CTG GCC GTG CTG CTG GTT TCC AGG GGC CAG CGG CGC CTG CGG GCC ATG        830
Leu Ala Val Leu Leu Val Ser Arg Gly Gln Arg Arg Leu Arg Ala Met
    240                 245                 250

CGG CTG GTG GTG GTG GTC GTG GTG GCC TTT GCC CTC TGC TGG ACC CCC        878
Arg Leu Val Val Val Val Val Val Ala Phe Ala Leu Cys Trp Thr Pro
255                 260                 265                 270

TAT CAC CTG GTG GTG CTG GTG GAC ATC CTC ATG GAC CTG GGC GCT TTG        926
Tyr His Leu Val Val Leu Val Asp Ile Leu Met Asp Leu Gly Ala Leu
                275                 280                 285

GCC CGC AAC TGT GGC CGA GAA AGC AGG GTA GAC GTG GCC AAG TCG GTC        974
Ala Arg Asn Cys Gly Arg Glu Ser Arg Val Asp Val Ala Lys Ser Val
            290                 295                 300

ACC TCA GGC CTG GGC TAC ATG CAC TGC TGC CTC AAC CCG CTG CTC TAT       1022
Thr Ser Gly Leu Gly Tyr Met His Cys Cys Leu Asn Pro Leu Leu Tyr
        305                 310                 315

GCC TTT GTA GGG GTC AAG TTC CGG GAG CGG ATG TGG ATG CTG CTC TTG       1070
Ala Phe Val Gly Val Lys Phe Arg Glu Arg Met Trp Met Leu Leu Leu
    320                 325                 330

CGC CTG GGC TGC CCC AAC CAG AGA GGG CTC CAG AGG CAG CCA TCG TCT       1118
```

-continued

```
Arg Leu Gly Cys Pro Asn Gln Arg Gly Leu Gln Arg Gln Pro Ser Ser
335                 340                 345                 350

TCC CGC CGG GAT TCA TCC TGG TCT GAG ACC TCA GAG GCC TCC TAC TCG      1166
Ser Arg Arg Asp Ser Ser Trp Ser Glu Thr Ser Glu Ala Ser Tyr Ser
                355                 360                 365

GGC TTG TGAGGCCGGA ATCCGGCTC CCCTTTCGCC ACAGTCTGA CTTCCCCGCA         1222
Gly Leu

TTCCAGGCTC CTCCCTCCCT CTGCCGGCTC TGGCTCTCCC CAATATCCTC GCTCCCGGGA    1282

CTCACTGGCA GCCCCAGCAC CACCAGGTCT CCCGGGAAGC CACCCTCCCA GCTCTGAGGA    1342

CTGCACCATT GCTGCTCCTT AGCTGCCAAG CCCCATCCTG CCGCCCGAGG TGGCTGCCTG    1402

GAGCCCCACT GCCTTCTCA TTTGGAAACT AAAACTTCAT CTTCCCCAAG TGCGGGAGT      1462

ACAAGGCATG GCGTAGAGGG TGCTGCCCCA TGAAGCCACA GCCCAGGCCT CCAGCTCAGC    1522

AGTGACTGTG GCCATGGTCC CCAAGACCTC TATATTTGCT CTTTTATTTT TATGTCTAAA    1582

ATCCTGCTTA AAACTTTTCA ATAAACAAGA TCGTCAGGAC CTTTTTTTTT TTTTTTTTTT    1642

TTTTTTTTTT TTTTTTTTTT TTTTTTTT                                      1670
```

(2) INFORMATION FOR SEQ ID NO:2:

(i) SEQUENCE CHARACTERISTICS:
        (A) LENGTH: 368 amino acids
        (B) TYPE: amino acid
        (D) TOPOLOGY: linear (ii) MOLECULE TYPE: protein (xi) SEQUENCE DESCRIPTION: SEQ ID NO:2:

```
Met Val Leu Glu Val Ser Asp His Gln Val Leu Asn Asp Ala Glu Val
1               5                   10                  15

Ala Ala Leu Leu Glu Asn Phe Ser Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala Leu Tyr Ser Leu Leu Phe
    50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
            100                 105                 110

Ala Ala Val Gln Trp Val Phe Gly Ser Gly Leu Cys Lys Val Ala Gly
        115                 120                 125

Ala Leu Phe Asn Ile Asn Phe Tyr Ala Gly Ala Leu Leu Leu Ala Cys
    130                 135                 140

Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175

Gly Leu Cys Leu Leu Phe Ala Leu Pro Asp Phe Ile Phe Leu Ser Ala
            180                 185                 190

His His Asp Glu Arg Leu Asn Ala Thr His Cys Gln Tyr Asn Phe Pro
        195                 200                 205

Gln Val Gly Arg Thr Ala Leu Arg Val Leu Gln Leu Val Ala Gly Phe
    210                 215                 220
```

```
Leu Leu Pro Leu Leu Val Met Ala Tyr Cys Tyr Ala His Ile Leu Ala
225                 230                 235                 240

Val Leu Leu Val Ser Arg Gly Gln Arg Arg Leu Arg Ala Met Arg Leu
                245                 250                 255

Val Val Val Val Val Ala Phe Ala Leu Cys Trp Thr Pro Tyr His
            260                 265                 270

Leu Val Val Leu Val Asp Ile Leu Met Asp Leu Gly Ala Leu Ala Arg
            275                 280                 285

Asn Cys Gly Arg Glu Ser Arg Val Asp Val Ala Lys Ser Val Thr Ser
290                 295                 300

Gly Leu Gly Tyr Met His Cys Cys Leu Asn Pro Leu Leu Tyr Ala Phe
305                 310                 315                 320

Val Gly Val Lys Phe Arg Glu Arg Met Trp Met Leu Leu Leu Arg Leu
                325                 330                 335

Gly Cys Pro Asn Gln Arg Gly Leu Gln Arg Gln Pro Ser Ser Ser Arg
                340                 345                 350

Arg Asp Ser Ser Trp Ser Glu Thr Ser Glu Ala Ser Tyr Ser Gly Leu
                355                 360                 365

(2) INFORMATION FOR SEQ ID NO:3:

(i) SEQUENCE CHARACTERISTICS:
        (A) LENGTH: 28 base pairs
        (B) TYPE: nucleic acid
        (C) STRANDEDNESS: single
        (D) TOPOLOGY: unknown (ix) FEATURE:
         (A) NAME/KEY: modified_base
         (B) LOCATION: 11
         (D) OTHER INFORMATION: /mod_base= i (ix) FEATURE:
         (A) NAME/KEY: modified_base
         (B) LOCATION: 12
         (D) OTHER INFORMATION: /mod_base= i (ix) FEATURE:
         (A) NAME/KEY: modified_base
         (B) LOCATION: 23
         (D) OTHER INFORMATION: /mod_base= i (ix) FEATURE:
         (A) NAME/KEY: modified_base
         (B) LOCATION: 26
         (D) OTHER INFORMATION: /mod_base= i (xi) SEQUENCE DESCRIPTION: SEQ ID NO:3:

GGGCTGCAGC NNTKKCMGAC MTNCTNYT                                                  28

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (ix) FEATURE:
         (A) NAME/KEY: modified_base
         (B) LOCATION: 10
         (D) OTHER INFORMATION: /mod_base= i (ix) FEATURE:
         (A) NAME/KEY: modified_base
         (B) LOCATION: 16
         (D) OTHER INFORMATION: /mod_base= i
```

```
    (ix) FEATURE:
        (A) NAME/KEY: modified_base
        (B) LOCATION: 18
        (D) OTHER INFORMATION: /mod_base= i (xi) SEQUENCE DESCRIPTION: SEQ ID NO:4:

GGGTCTAGAN GGGTTNANRC ARCWRYG                                                    27
```

METHOD FOR IDENTIFYING LIGANDS, INHIBITORS OR PROMOTERS OF CXC CHEMOKINE RECEPTOR 3

This application is a continuation of U.S. application Ser. No. 08/709,838, filed Sep. 10, 1996, now U.S. patent Ser. No. 6,140,064.

BACKGROUND

Chemokines constitute a family of small cytokines that are produced in inflammation and regulate leukocyte recruitment (Baggiolini, M. et al., "Interleukin-8 and related chemotactic cytokines—CXC and CC chemokines," *Adv. Immunol.* 55: 97–179 (1994); Springer, T. A., "Traffic signals on endothelium for lymphocyte recirculation and leukocyte emigration," *Annu. Rev. Physiol.* 57: 827–872 (1995); and Schall, T. J. and K. B. Bacon, "Chemokines, leukocyte trafficking, and inflammation," *Curr. Opin. Immunol.* 6: 865–873 (1994)). Chemokines are capable of selectively inducing chemotaxis of the formed elements of the blood (other than red blood cells), including leukocytes such as neutrophils, monocytes, macrophages, eosinophils, basophils, mast cells, and lymphocytes, such as T cells and B cells. In addition to stimulating chemotaxis, other changes can be selectively induced by chemokines in responsive cells, including changes in cell shape, transient rises in the concentration of intracellular free calcium ions ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

Two subfamilies of chemokines, designated as CXC and CC chemokines, are distinguished by the arrangement of the first two of four conserved cysteine residues, which are either separated by one amino acid (as in CXC chemokines IL-8, γIP-10, Mig, PF4, ENA-78, GCP-2, GROα, GROβ, GROγ, NAP-2, NAP-4) or are adjacent residues (as in CC chemokines MIP-1α, MIP-1β, RANTES, MCP-1, MCP-2, MCP-3, I-309). Most CXC chemokines attract neutrophil leukocytes. For example, the CXC chemokines interleukin 8 (IL-8), platelet factor 4 (PF4), and neutrophil-activating peptide 2 (NAP-2) are potent chemoattractants and activators of neutrophils. The CXC chemokines designated Mig (monokine induced by gamma interferon) and IP-10 (γIP-10, interferon-gamma inducible 10 kDa protein) are particularly active in inducing chemotaxis of activated peripheral blood leukocytes. CC chemokines are generally less selective and can attract a variety of leukocyte cell types, including monocytes, eosinophils, basophils, T lymphocytes and natural killer cells. CC chemokines such as human monocyte chemotactic proteins 1–3 (MCP-1, MCP-2 and MCP-3), RANTES (Regulated on Activation, Normal T Expressed and Secreted), and the macrophage inflammatory proteins 1α and 1β (MIP-1α and MIP-1β) have been characterized as chemoattractants and activators of monocytes or lymphocytes, but do not appear to be chemoattractants for neutrophils.

Chemokines act through receptors which belong to a superfamily of seven transmembrane spanning G-protein coupled receptors (Murphy, P. M., "The molecular biology of leukocyte chemoattractant receptors," *Annu. Rev. Immunol.,* 12: 593–633 (1994); Gerard, C. and N. P. Gerard, "The pro-inflammatory seven transmembrane segment receptors of the leukocyte," *Curr. Opin. Immunol.,* 6: 140–145 (1994)). This family of G-protein coupled (serpentine) receptors comprises a large group of integral membrane proteins, containing seven transmembrane-spanning regions. The receptors are coupled to G proteins, which are heterotrimeric regulatory proteins capable of binding GTP and mediating signal transduction from coupled receptors, for example, by the production of intracellular mediators. Two of these receptors, the interleukin-8 (IL-8) receptors, IL-8R1 (interleukin-8 receptor type 1; Holmes, W. E. et al., "Structure and functional expression of a human interleukin-8 receptor," *Science,* 253: 1278–1280 (1991)) and IL-8R2 (interleukin-8 receptor type 1; Murphy, P. M. and H. L. Tiffany, "Cloning of complementary DNA encoding a functional human interleukin-8 receptor," *Science,* 253: 1280–1283 (1991)), are largely restricted to neutrophils and recognize the NH2-terminal Glu-Leu-Arg (ELR) motif, an essential binding epitope in those CXC chemokines that induce neutrophil chemotaxis (Clark-Lewis, I. et al., "Structure-activity relationships of interleukin-8 determined using chemically synthesized analogs. Critical role of NH2-terminal residues and evidence for uncoupling of neutrophil chemotaxis, exocytosis, and receptor binding activities," *J. Biol. Chem.,* 266: 23128–23134 (1991); Hébert, C. A. et al., "Scanning mutagenesis of interleukin-8 identifies a cluster of residues required for receptor binding," *J. Biol. Chem.,* 266: 18989–18994 (1991); and Clark-Lewis, I. et al., "Platelet factor 4 binds to interleukin 8 receptors and activates neutrophils when its N terminus is modified with Glu-Leu-Arg," *Proc. Natl. Acad. Sci. USA,* 90: 3574–3577 (1993)). Five distinct CC chemokine receptors have been described, and are designated CC-CKR1, –2, –3, –4 and –5 (CC-CKR, CC chemokine receptor; Neote, K. et al., "Molecular cloning, functional expression, and signaling characteristics of a CC chemokine receptor," *Cell,* 72: 415–425 (1993); Gao, J.-L. et al., "Structure and functional expression of the human macrophage inflammatory protein 1α/RANTES receptor," *J. Exp. Med.,* 177: 1421–1427 (1993); Charo, I. F. et al., "Molecular cloning and functional expression of two monocyte chemoattractant protein 1 receptors reveals alternative splicing of the carboxyl-terminal tails," *Proc. Natl. Acad. Sci. USA,* 91: 2752–2756 (1994); Myers, S. J., et al., *J. Biol. Chem.,* 270: 5786–5792 (1995); Combadiere, C. et al., Cloning and functional expression of a human eosinophil CC chemokine receptor," *J. Biol. Chem.,* 270 (27): 16491–16494 (1995); and Correction, *J. Biol. Chem.,* 270: 30235 (1995); Ponath, P. D. et al., "Molecular cloning and characterization of a human eotaxin receptor expressed selectively on eosinophils," *J. Exp. Med.,* 183: 2437–2448 (1996); and Daugherty, B. L. et al., "Cloning, expression, and characterization of the human eosinophil eotaxin receptor," *J. Exp. Med.,* 183: 2349–2354 (1996); Power, C. A. et al., 1995, "Molecular cloning and functional expression of a novel CC chemokine receptor cDNA from a human basophilic cell line," *J. Biol. Chem.,* 270: 19495–19500 (1995); Hoogewerf, A. J. et al., "Molecular cloning of murine CC CKR-4 and high affinity binding of chemokines to murine and human CC CKR-4," *Biochem. Biophys. Res. Commun.,* 218: 337–343 (1996); Samson, M. et al., "Molecular cloning and functional expression of a new human CC-chemokine receptor gene," *Biochemistry,* 35: 3362–3367 (1996)). The CC chemokine receptors occur on several types of leukocytes, including monocytes, granulocytes and lymphocytes, and recognize CC chemokines, but not CXC chemokines.

In contrast to monocytes and granulocytes, lymphocyte responses to chemokines are not well understood. Notably, none of the receptors of known specificity appear to be restricted to lymphocytes and the chemokines that recognize these receptors cannot, therefore, account for events such as the selective recruitment of T lymphocytes that is observed in T cell-mediated inflammatory conditions. Moreover, although a number of proteins with significant sequence similarity and similar tissue and leukocyte subpopulation distribution to known chemokine receptors have been identified and cloned, the ligands for these receptors remain undefined. Thus, these proteins are referred to as orphan receptors. The characterization of the ligand(s) of a receptor, is essential to an understanding of the interaction of chemokines with their target cells, the events stimulated by this interaction, including chemotaxis and cellular activation of leukocytes, and the development of therapies based upon modulation of receptor function.

SUMMARY OF THE INVENTION

The present invention relates to proteins or polypeptides, referred to herein as isolated and/or recombinant mammalian (e.g., a primate such as a human) IP-10/Mig receptor proteins designated CXC Chemokine Receptor 3 (CXCR3) and variants thereof. Recombinant CXCR3 proteins and variants can be produced in host cells as described herein. In one embodiment, a CXCR3 protein or variant thereof is characterized by selective binding (e.g., high affinity binding) of one or more chemokines, such as IP-10 and/or Mig, and/or the ability to induce a (one or more) cellular response(s) (e.g., chemotaxis, exocytosis, release of one or more inflammatory mediators).

Another aspect of the present invention relates to isolated and/or recombinant nucleic acids which encode a mammalian (e.g., a primate such as a human) CXCR3 protein or variant thereof. The invention further relates to recombinant nucleic acid constructs, such as plasmids or retroviral vectors, which contain a nucleic acid which encodes a protein of the present invention or a variant thereof. The nucleic acids and constructs can be used to produce recombinant receptor proteins and host cells comprising a construct. In another embodiment, the nucleic acid encodes an antisense nucleic acid which can hybridize with a second nucleic acid encoding a CXCR3 protein and which, when introduced into cells, can inhibit the expression of receptor.

Antibodies reactive with CXCR3 receptors can be produced using the proteins or variants thereof (e.g., a peptide) or cells expressing receptor protein or variant as immunogen, for example. Such antibodies or fragments thereof are useful in therapeutic, diagnostic and research applications, including the purification and study of the receptor proteins, identification of cells expressing surface receptor, and sorting or counting of cells.

Also encompassed by the present invention are methods of identifying ligands of the receptor, inhibitors (e.g., antagonists) or promoters (e.g., agonists) of receptor function. In one embodiment, suitable host cells which have been engineered to express a receptor protein or variant encoded by a nucleic acid introduced into said cells are used in an assay to identify and assess the efficacy of ligands, inhibitors or promoters of receptor function. Such cells are also useful in assessing the function of the expressed receptor protein or polypeptide.

According to the present invention, ligands, inhibitors and promoters of receptor function can be identified in a suitable assay, and further assessed for therapeutic effect. Inhibitors of receptor function can be used to inhibit (reduce or prevent) receptor activity, and ligands and/or promoters can be used to induce (trigger or enhance) normal receptor function where indicated. Thus, the present invention provides a method of treating inflammatory diseases including autoimmune disease and graft rejection, comprising administering an inhibitor of receptor function to an individual (e.g., a mammal). The present invention further provides a method of stimulating receptor function by administering a ligand or promoter to an individual, providing a new approach to selective stimulation of leukocyte function, which is useful, for example, in the treatment of infectious diseases and cancer.

BRIEF DESCRIPTION OF THE DRAWINGS

FIG. 1 is an illustration of the nucleotide sequence determined from the 1670 bp insert of a cDNA encoding a human IP-10/Mig receptor, which was isolated from a human CD4+ T cell (KT30) cDNA library (SEQ ID NO:1). An open reading frame (69–1175) encodes a predicted protein of 368 amino acids (SEQ ID NO:2). A putative poly-A signal and poly A site are located at positions 1534–1539 and at 1624–1670, respectively.

FIG. 2 is an illustration of the conceptual translation of the open reading frame of the sequence in FIG. 1, which encodes a human IP-10/Mig receptor (SEQ ID NO:2). Arrowheads indicate potential N-linked glycosylation sites and horizontal lines indicate the location of putative transmembrane domains (TM1–TM7).

FIG. 3A is a graph illustrating the concentration dependent $[Ca^{2+}]_i$ changes in IP-10/MigR-transfected 300–19 cells. IP-10 or Mig were each added at 1, 10, and 100 nM to Fura-2/AM loaded cells (arrowhead), and $[Ca^{2+}]_i$-dependent fluorescence changes were recorded. Non-transfected cells (lower tracings) were stimulated with IP-10 or Mig at 100 nM under identical conditions.

FIG. 3B is a graph illustrating the results of studies assessing receptor desensitization and cross-desensitization, in which IP-10/MigR expressing 300–19 cells were sequentially stimulated with 100 nM IP-10 or Mig, and with IP-10 followed by Mig or vice versa, and fluorescence changes were recorded.

FIG. 3C is a graph illustrating the chemotaxis of IP-10/MigR expressing Jurkat cells stimulated with IP-10 (filled circles) or Mig (filled squares). The lower panel shows the response of non-transfected Jurkat cells when stimulated with increasing amounts of IP-10 (open circles) or Mig (open squares). Mean numbers (±SD) of migrating cells per five high power fields are presented.

FIG. 4A is a graph illustrating $[Ca^{2+}]_i$ changes induced by IP-10 or Mig. IP-10 or Mig were each added at 1, 10, and 100 nM to Fura-2/AM loaded cultured cells (arrowhead), and $[Ca^{2+}]_i$-dependent fluorescence changes were recorded (upper tracings). Freshly isolated cells (lower tracings) were stimulated with IP-10 or Mig at 100 nM under the same conditions.

FIG. 4B is a graph illustrating chemotaxis of PBL in response to increasing concentrations of IP-10 (filled circles) or Mig (filled squares) (mean numbers (±SD) of migrating cells per five high power fields are presented).

DETAILED DESCRIPTION OF THE INVENTION

Figures 3A, 3B, 3C:
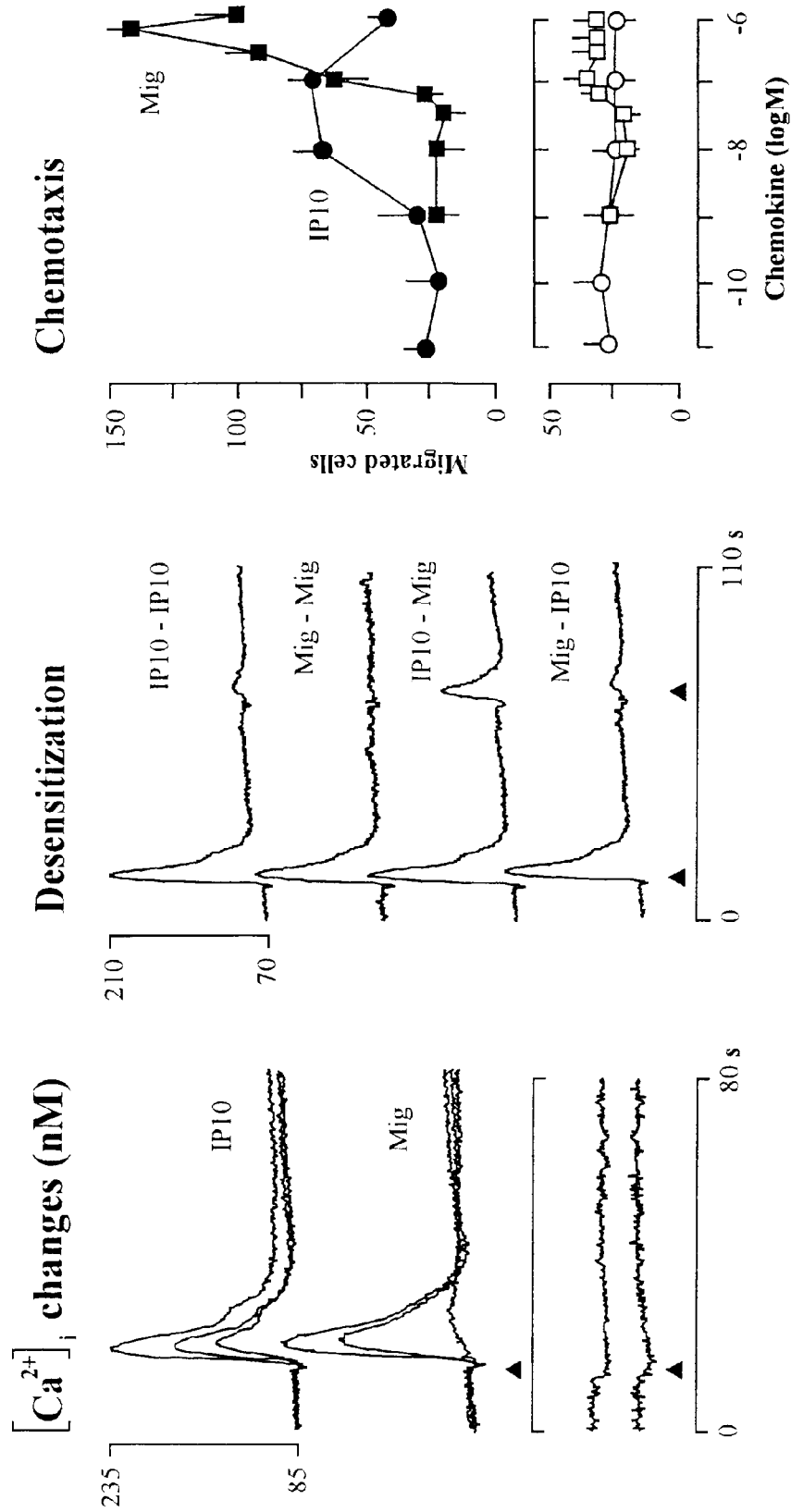
FIGS. 3A–3C are graphs illustrating the responses induced by IP-10 and Mig in stably transfected cells expressing IP-10/MigR.

As described herein, a nucleic acid encoding a novel chemokine receptor that is selective for the CXC chemokines IP-10 and Mig was cloned and characterized. The clone, which was isolated from a human CD4$^+$ T cell library, was not detected in monocyte- or granulocyte-derived cDNA libraries. Sequence analysis of the clone revealed an open reading frame of 1104 base pairs (FIG. 1, SEQ ID NO:1), encoding a predicted protein of 368 amino acids with a predicted molecular mass of 40,659 daltons (FIG. 2, SEQ ID NO:2). The amino acid sequence includes seven putative transmembrane segments which are characteristic of G-protein coupled receptors and are found in other chemoattractant receptors. Consistent with this observation, the receptor mediates Ca$^{2+}$ (calcium ion) mobilization and chemotaxis in response to IP-10 and Mig (Example 2). No significant response to the CXC chemokines IL-8, GROα, NAP-2 (neutrophil-activating protein-2), GCP-2 (granulocyte chemotactic protein-2), ENA78 (epithelial-derived neutrophil-activating peptide 78), PF4 (platelet factor 4), or the CC chemokines MCP-1 (monocyte chemotactic protein-1), MCP-2, MCP-3, MCP-4, MIP-1α(macrophage inflammatory protein-1α), MIP-1β, RANTES (regulated on activation, normal T cell expressed and secreted), I309, eotaxin or lymphotactin was detected under similar conditions.

The restricted expression of human CXCR3 in activated T lymphocytes and the ligand selectivity of the receptor for IP-10 and Mig are noteworthy. The human receptor is highly expressed in IL-2 activated T lymphocytes, but was not detected in resting T lymphocytes, B lymphocytes, monocytes or granulocytes under the conditions used (Example 2). The selective expression in activated T lymphocytes is of interest, because other receptors for chemokines which have been reported to attract lymphocytes (e.g., MCP-1, MCP-2, MCP-3, MIP-1α, MIP-1βand RANTES) are also found in granulocytes, such as neutrophils, eosinophils and basophils, as well as monocytes. These results suggest that the IP-10/Mig receptor designated CXCR3 is involved in the selective recruitment of effector T cells.

The receptor recognizes two unusual CXC chemokines, designated IP-10 and Mig. Although IP-10 and Mig both belong to the CXC subfamily, in contrast to IL-8 and other CXC chemokines which are potent chemoattractants for neutrophils, the primary targets of IP-10 and Mig are lymphocytes, particularly effector cells such as activated or stimulated T lymphocytes and natural killer (NK) cells (Taub, D. D. et al., *J. Exp. Med.*, 177: 18090–1814 (1993); Taub, D. D. et al., *J. Immunol.*, 155: 3877–3888 (1995)). (NK cells are large granular lymphocytes, which lack a specific T cell receptor for antigen recognition, but possess cytolytic activity against cells such as tumor cells and virally infected cells.) Consistently, IP-10 and Mig lack the ELR motif, an essential binding epitope in those CXC chemokines that efficiently induce neutrophil chemotaxis (Clark-Lewis, I. et al., *J. Biol. Chem.*, 266: 23128–23134 (1991); Hébert, C. A. et al., *J. Biol. Chem.*, 266: 18989–18994 (1991); and Clark-Lewis, I. et al., *Proc. Natl. Acad. Sci. USA*, 90: 3574–3577 (1993)). In addition, both recombinant human Mig and recombinant human IP-10 have been reported to induce calcium flux in tumor infiltrating lymphocytes (TIL) (Liao, F. et al., *J. Exp. Med.*, 182: 1301–1314 (1995)). While IP-10 has been reported to induce chemotaxis of monocytes in vitro (Taub, D. D. et al., *J. Exp. Med.*, 177: 1809–1814 (1993), the receptor responsible has not been identified), human Mig appears highly selective, and does not show such an effect (Liao, F. et al., *J. Exp. Med.*, 182: 1301–1314 (1995)). IP-10 expression is induced in a variety of tissues in inflammatory conditions such as psoriasis, fixed DRUG eruptions, cutaneous delayed-type hypersensitivity responses, tuberculoid leprosy, and in experimental glomerulonephritis, and experimental allergic encephalomyelitis. IP-10 also has a potent in vivo antitumor effect that is T cell dependent, is reported to be an inhibitor of angiogenesis in vivo, and can induce chemotaxis and degranulation of NK cells in vitro, suggesting a role as a mediator of NK cell recruitment and degranulation (in tumor cell destruction, for example) (Luster, A. D. and P. Leder, *J. Exp. Med.*, 178: 1057–1065 (1993); Luster, A. D. et al., *J. Exp. Med.* 182: 219–231 (1995); Angiolillo, A. L. et al., *J. Exp. Med.*, 182: 155–162 (1995); Taub, D. D. et al., *J. Immunol.*, 155: 3877–3888 (1995)).

The expression patterns of IP-10 and Mig are also distinct in that expression of each is induced by interferon-gamma (IFNγ), while the expression of IL-8 is down-regulated by IFNγ (Luster, A. D. et al., *Nature*, 315: 672–676 (1985); Farber, J. M., *Proc. Natl. Acad. Sci. USA*, 87: 5238–5242 (1990); Farber, J. M., *Biochem. Biophys. Res. Commun.*, 192 (1): 223–230 (1993), Liao, F. et al., *J. Exp. Med.*, 182: 1301–1314 (1995); Seitz, M. et al., "Enhanced production of neutrophil-activating peptide-1/interleukin-8 in rheumatoid arthritis," *J. Clin. Invest.*, 87: 463–469 (1991); Galy, A. H. M. and H. Spits, "IL-1, IL-4, and IFN-gamma differentially regulate cytokine production and cell surface molecule expression in cultured human thymic epithelial cells," *J. Immunol.*, 147: 3823–3830 (1991)).

Chemokines have been recently recognized as the long-sought mediators for the recruitment of lymphocytes. Several CC chemokines were found to elicit lymphocyte chemotaxis (Loetscher, P. et al., "The monocyte chemotactic proteins, MCP-1, MCP-2 and MCP-3, are major attractants for human CD4$^+$ and CD8$^+$T lymphocytes," *FASEB J.*, 8: 1055–1060 (1994)), but they are also active on granulocytes and monocytes (Uguccioni, M. et al., "Actions of the chemotactic cytokines MCP-1, MCP-2, MCP-3, RANTES, MIP-1αand MIP-1β on human monocytes," *Eur. J. Immunol.*, 25: 64–68 (1995); Baggiolini, M. and C. A. Dahinden, "CC chemokines in allergic inflammation," *Immunol. Today*, 15: 127–133 (1994)). The situation is different for IP-10 and Mig, which are selective in their action on lymphocytes, including activated T lymphocytes and NK cells, and which bind CXCR3, a receptor which does not recognize numerous other chemokines and which displays a selective pattern of expression (Example 2).

In view of these observations, it is reasonable to conclude that the formation of the characteristic infiltrates in delayed-type hypersensitivity lesions, sites of viral infection, and certain tumors is a process mediated by via CXCR3 and regulated by CXCR3 expression. Lymphocytes, particularly T lymphocytes, bearing a CXCR3 receptor as a result of activation can be recruited into inflammatory lesions, sites of infection, or tumors by IP-10 and/or Mig, which can be induced locally by interferon-gamma. Thus, CXCR3 plays a role in the selective recruitment of lymphocytes, particularly effector cells such as activated or stimulated T lymphocytes.

Proteins and Peptides

The present invention relates to isolated and/or recombinant (including, e.g., essentially pure) proteins or polypeptides designated mammalian CXCR3 proteins and variants thereof. In a preferred embodiment, the isolated and/or recombinant proteins of the present invention have at least one property, activity or function characteristic of a mammalian CXCR3 protein (as defined herein), such as a binding activity (e.g., ligand, inhibitor and/or promoter binding), a signalling activity (e.g., activation of a mammalian G protein, induction of rapid and transient increase in the concentration of cytosolic free calcium $[Ca^{2+}]_i$), cellular response function (e.g., stimulation of chemotaxis, exocytosis or inflammatory mediator release by leukocytes), and/or an immunological property as defined herein. For example, some proteins of the present invention can selectively bind to IP-10 and/or Mig, mediate cellular signalling and/or a response thereto in vitro and/or in vivo (e.g., calcium flux, chemotaxis and/or degranulation especially of activated T lymphocytes). For example, as shown herein, a human CXCR3 protein, produced in mammalian cells by expression of a cDNA clone, can selectively bind to CXC chemokines IP-10 and/or Mig, and mediate signalling, and a cellular response (e.g., chemotaxis). In one embodiment, proteins of the present invention can bind a CXC chemokine from the same or a different mammalian species (e.g., human IP-10, murine IP-10, human Mig, murine Mig) (human IP-10, Luster, A. D. et al., *Nature*, 315: 672–676 (1985); murine IP-10 (also referred to as CRG-2), Vanguri, P. and J. M. Farber, *J. Biol. Chem.*, 265: 15049 (1990) and Luster, A. D. and P. Leder, *J. Exp. Med.*, 178: 1057–1065 (1993); murine Mig, Farber, J. M., *Proc. Natl. Acad. Sci. USA*, 87: 5238–5242 (1990); human Mig, Farber, J. M., *Biochem. Biophys. Res. Commun.*, 192 (1): 223–230 (1993) and Liao, F. et al., *J. Exp. Med.*, 182: 1301–1314 (1995)).

Proteins or polypeptides referred to herein as "isolated" are proteins or polypeptides purified to a state beyond that in which they exist in mammalian cells, and include proteins or polypeptides obtained by methods described herein, similar methods or other suitable methods, including essentially pure proteins or polypeptides, proteins or polypeptides produced by chemical synthesis (e.g., synthetic peptides), or by combinations of biological and chemical methods, and recombinant proteins or polypeptides which are isolated. The proteins can be obtained in an isolated state of at least about 50% by weight, preferably at least about 75% by weight, or in essentially pure form. Proteins or polypeptides referred to herein as "recombinant" are proteins or polypeptides produced by the expression of recombinant nucleic acids.

As used herein "mammalian CXCR3 protein" refers to naturally occurring or endogenous mammalian CXCR3 proteins and to proteins having an amino acid sequence which is the same as that of a naturally occurring or endogenous corresponding mammalian CXCR3 protein (e.g., recombinant proteins). Accordingly, as defined herein, the term includes mammalian CXCR3 protein, including mature protein, polymorphic or allelic variants, and other isoforms of mammalian CXCR3 (e.g., produced by alternative splicing or other cellular processes), and modified or unmodified forms of the foregoing (e.g., glycosylated, unglycosylated, phosphorylated or unphosphorylated CXCR3 proteins). Naturally occurring or endogenous mammalian CXCR3 proteins include wild type proteins such as mature CXCR3, polymorphic or allelic variants and other isoforms which occur naturally in mammals (e.g., humans, non-human primates). Such proteins can be recovered from a source which naturally produces mammalian CXCR3, for example. These proteins and mammalian CXCR3 proteins having the same amino acid sequence as a naturally occurring or endogenous corresponding mammalian CXCR3, are referred to by the name of the corresponding mammal. For example, where the corresponding mammal is a human, the protein is designated as a human CXCR3 protein (e.g., a recombinant human CXCR3 produced in a suitable host cell).

"Functional variants" of mammalian CXCR3 proteins include functional fragments, functional mutant proteins, and/or functional fusion proteins (e.g., produced via mutagenesis and/or recombinant techniques). Generally, fragments or portions of mammalian CXCR3 proteins encompassed by the present invention include those having a deletion (i.e., one or more deletions) of an amino acid (i.e., one or more amino acids) relative to the mature mammalian CXCR3 protein (such as N-terminal, C-terminal or internal deletions). Fragments or portions in which only contiguous amino acids have been deleted or in which non-contiguous amino acids have been deleted relative to mature mammalian CXCR3 protein are also envisioned.

Generally, mutants or derivatives of mammalian CXCR3 proteins, encompassed by the present invention include natural or artificial variants differing by the addition, deletion and/or substitution of one or more contiguous or non-contiguous amino acid residues, or modified polypeptides in which one or more residues is modified, and mutants comprising one or more modified residues. Preferred mutants are natural or artificial variants of mammalian CXCR3 proteins differing by the addition, deletion and/or substitution of one or more contiguous or non-contiguous amino acid residues. Such mutations can be in a conserved region or nonconserved region (compared to other CXC and/or CC chemokine receptors), extracellular, cytoplasmic, or transmembrane region, for example.

A "functional fragment or portion", "functional mutant" and/or "functional fusion protein" of a mammalian CXCR3 protein refers to an isolated and/or recombinant protein or oligopeptide which has at least one property, activity or function characteristic of a mammalian CXCR3 receptor (as defined herein), such as a binding activity (e.g., ligand, inhibitor and/or promoter binding), a signalling activity (e.g., activation of a mammalian G protein, induction of rapid and transient increase in the concentration of cytosolic free calcium $[Ca^{2+}]_i$), cellular response function (e.g., stimulation of chemotaxis, exocytosis or inflammatory mediator release by leukocytes), and/or an immunological property as defined herein.

As used herein, a protein or polypeptide having "at least one immunological property" of a mammalian CXCR3 protein is one which (a) is bound by at least one antibody of a selected epitopic specificity which binds to a naturally occurring or endogenous mammalian CXCR3 protein or to a protein having the same amino acid seqence as the naturally occurring or endogenous mammalian CXCR3 protein (e.g., human CXCR3), and/or (b) is an immunogen capable of inducing the formation in a suitable animal of an antibody of a selected epitopic specificity which binds to a naturally occurring or endogenous mammalian CXCR3 or to a protein having the same amino acid seqence as the naturally occurring or endogenous mammalian CXCR3. For example, a suitable fragment can cross-react with an antibody which is raised against and/or reactive with isolated mammalian CXCR3.

Suitable fragments or mutants can be identified by screening. For example, the N-terminal, C-terminal, or internal regions of the protein can be deleted in a step-wise fashion and the resulting protein or polypeptide can be screened using a suitable assay, such as an assay described herein (e.g., chemotaxis, calcium flux). Where the resulting protein displays activity in the assay, the resulting protein ("fragment") is functional. Information regarding the structure and function of mammalian G protein coupled receptors, including CXC chemokine and CC chemokine receptors, provides a basis for dividing mammalian CXCR3 proteins into functional domains (Murphy, P. M., "The molecular biology of leukocyte chemoattractant receptors," *Annu. Rev. Immunol.*, 12: 593–633 (1994) and Gerard, C. and N. P. Gerard, "The pro-inflammatory seven transmembrane segment receptors of the leukocyte," *Curr. Opin. Immunol.*, 6: 140–145 (1994), and references cited therein).

The term variant also encompasses fusion proteins, comprising a mammalian CXCR3 proteins (e.g., human CXCR3) as a first moiety, linked to a second moiety not occurring in the mammalian CXCR3 as found in nature. Thus, the second moiety can be an amino acid, oligopeptide or polypeptide. The first moiety can be in an N-terminal location, C-terminal location or internal to the fusion protein. In one embodiment, the fusion protein comprises an affinity ligand (e.g., an enzyme, an antigen, epitope tag) as the first moiety, and a second moiety comprising a linker sequence and human CXCR3 or portion thereof.

Examples of mammalian CXCR3 proteins include proteins encoded by a nucleic acid of the present invention, such as a protein having an amino acid sequence as set forth or substantially as set forth in FIG. 2 (SEQ ID NO:2). In a preferred embodiment, a mammalian CXCR3 or variant (e.g., a variant including the extracellular N-terminal segment) has an amino acid sequence which is at least about 50% identical, more preferably at least about 70% identical, and still more preferably at least about 80% identical, to the protein shown in FIG. 2 (SEQ ID NO:2).

It will be appreciated that isolated and/or recombinant mammalian CXCR3 proteins and variants thereof can be modified, for example, by incorporation of or attachment (directly or indirectly (e.g., via a linker)) of a detectable label such as a radioisotope, spin label, antigen (e.g., epitope label such as a FLAG tag) or enzyme label, flourescent or chemiluminesent group and the like, and such modified forms are included within the scope of the invention.

Nucleic Acids, Constructs and Vectors

The present invention relates to isolated and/or recombinant (including, e.g., essentially pure) nucleic acids having sequences which encode a mammalian (e.g., human) CXCR3 protein or variant thereof as described herein. Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

In one embodiment, the nucleic acid or portion thereof encodes a protein or polypeptide having at least one function characteristic of a mammalian CXCR3 protein (e.g., a human CXCR3 receptor), such as a binding activity (e.g., ligand, inhibitor and/or promoter binding), a signalling activity (e.g., activation of a mammalian G protein, induction of rapid and transient increase in the concentration of cytosolic free calcium $[Ca^{2+}]_i$), and/or stimulation of a cellular response (e.g., stimulation of chemotaxis, exocytosis or inflammatory mediator release by leukocytes). The present invention also relates more specifically to isolated and/or recombinant nucleic acids or a portion thereof comprising sequences which encode a mammalian CXCR3 receptor or a portion thereof. The present invention relates even more specifically to isolated and/or recombinant nucleic acids comprising sequences which encode a human CXCR3 protein.

The invention further relates to isolated and/or recombinant nucleic acids, including double or single stranded DNA or RNA, that are characterized by (1) their ability to hybridize to: (a) a nucleic acid having the sequence SEQ ID NO:1, (b) a nucleic acid having a sequence which is complementary to SEQ ID NO:1, or (c) a portion of the foregoing comprising the open reading frame of SEQ ID NO:1 (a portion of the strand illustrated in FIG. 1 or the corresponding portion of the complementary strand); and/or (2) by their ability to encode a polypeptide having the amino acid sequence SEQ ID NO:2 or a functional equivalent thereof (i.e., a polypeptide having ligand binding activity for one or more natural or physiological ligand(s) of the receptor and/or stimulatory function responsive to ligand binding, such that it can induce a cellular response (e.g., induction (including triggering or stimulation) of chemotaxis, exocytosis or inflammatory mediator release by leukocytes); and/or (3) by both characteristics.

In one embodiment, the percent amino acid sequence identity between SEQ ID NO:2 and functional equivalents thereof is at least about 60% ($\geq$60%). In a preferred embodiment, functional equivalents of SEQ ID NO:2 share at least about 70% sequence identity with SEQ ID NOS:2. More preferably, the percent amino acid sequence identity between SEQ ID NO:2 and functional equivalents thereof is at least about 80%, and still more preferably, at least about 90%.

Isolated and/or recombinant nucleic acids meeting these criteria comprise nucleic acids having sequences identical to sequences of naturally occurring mammalian CXCR3 receptors and portions thereof, or variants of the naturally occurring sequences. Such variants include mutants differing by the addition, deletion or substitution of one or more residues, modified nucleic acids in which one or more residues is modified (e.g., DNA or RNA analogs), and mutants comprising one or more modified residues. In one embodiment, the nucleic acid shares at least about 50% nucleotide sequence similarity, more preferably at least about 75% nucleotide sequence similarity, and still more preferably at least about 90% nucleotide sequence similarity, with one strand of the sequence illustrated in SEQ ID NO:1 or to the coding region thereof. Preferred nucleic acids have lengths of at least about 40 nucleotides, more preferably at least about 50, and still more preferably at least about 75 nucleotides.

Such nucleic acids can be detected and isolated by hybridization under high stringency conditions or moderate stringency conditions, for example. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M. et al., eds., Vol. 1, Suppl. 26, 1991), the teachings of which are incorporated herein by reference. Factors such as probe length, base composition, percent mismatch between the hybridizing sequences, temperature and ionic strength influence the stability of nucleic acid hybrids. Thus, high or moderate stringency conditions can be determined empirically.

Isolated and/or recombinant nucleic acids that are characterized by their ability to hybridize to a nucleic acid having the sequence SEQ ID NO:1 or the complement thereof (e.g., under high or moderate stringency conditions) may further encode a protein or polypeptide having at least one function characteristic of a mammalian CXCR3 protein (e.g., a human CXCR3 protein), such as a binding activity (e.g., ligand, inhibitor and/or promoter binding), a signalling activity (e.g., activation of a mammalian G protein, induction of rapid and transient increase in the concentration of cytosolic free calcium $[Ca^{2+}]_i$), and/or stimulation of a cellular response (e.g., stimulation of chemotaxis, exocytosis or inflammatory mediator release by leukocytes).

The human CXCR3 nucleic acid described herein, or sufficient portions thereof, whether isolated, recombinant and/or synthetic, including fragments produced by PCR, can be used as probes or primers to detect and/or recover nucleic acids (e.g., genomic DNA, allelic variants, cDNA) encoding CXCR3 receptors (homologs) or other related receptor genes (e.g., novel CXC chemokine receptor genes) from other mammalian species including, but not limited to primates (e.g., a primate other than a human, such as a monkey (e.g., cynomolgus monkey)), bovine, ovine, equine, canine, feline and rodent (e.g., guinea pig, murine species such as rat, mouse). This can be achieved using the procedures described herein or other suitable methods, including hybridization, PCR or other suitable techniques. Mammalian nucleic acids can be used to prepare constructs (e.g., vectors), receptor or fragments thereof, and host strains useful in the production and methods of use of receptor.

In one embodiment, a nucleic acid encoding a mammalian CXCR3 protein (or variant) is producible by methods such as PCR amplification. For example, appropriate primers (e.g., a pair of primers or nested primers) can be designed which comprise a sequence which is complementary or substantially complementary to a portion of the human CXCR3 cDNA described herein. For instance, primers complementary to the 5'- or 3'-ends of the coding sequence and/or flanking the coding sequence can be designed. Such primers can be used in a polymerase chain reaction with a suitable template nucleic acid to obtain nucleic acid encoding a mammalian CXCR3, for example. Suitable templates include e.g., constructs described herein (such as pcDNA3-Clone8), a cDNA or genomic library or another suitable source of mammalian (e.g., a human, primate) cDNA or genomic DNA. Primers can contain portions complementary to flanking sequences of a construct selected as template as appropriate.

The binding function of a protein or polypeptide (e.g., encoded by hybridizing nucleic acid) can be detected in binding or binding inhibition assays, using membrane fractions containing receptor or cells expressing receptor, for example (see e.g., Van Riper et al., *J. Exp. Med.*, 177: 851–856 (1993); Sledziewski et al., U.S. Pat. No. 5,284,746 (Feb. 8, 1994)). Thus, the ability of the encoded protein or polypeptide to bind a ligand, such as IP-10 or Mig, an inhibitor and/or promoter, can be assessed. The antigenic properties of proteins or polypeptides encoded by nucleic acids of the present invention can be determined by immunological methods employing antibodies that bind to a mammalian CXCR3, such as immunoblotting, immunoprecipitation and immunoassay (e.g., radioimmunoassay, ELISA).

The signalling function of a protein or polypeptide (e.g., encoded by hybridizing nucleic acid) can be detected by enzymatic assays for G protein activity responsive to receptor binding (e.g., exchange of GTP for GDP on the G protein α subunit, using membrane fractions). G protein coupling can be further assessed, for example, using assays in which stimulation by G protein is blocked by treatment or pretreatment of cells or a suitable cellular fraction (e.g., membranes) with specific inhibitors of G proteins, such as *Bordetella pertussis* toxin (Bischoff, S. C. et al., *Eur. J. Immunol.*, 23: 761–767 (1993); Sozzani, S. et al., *J. Immunol.*, 147: 2215–2221 (1991)).

The stimulatory function of a protein or polypeptide (e.g., encoded by hybridizing nucleic acid) can be detected by standard assays for chemotaxis or mediator release, using cells expressing the protein or polypeptide (e.g., assays which monitor chemotaxis, exocytosis (e.g., degranulation of enzymes, such as esterases (e.g., serine esterases), perforin, granzymes) or mediator release (e.g., histamine, leukotriene) in response to a ligand (e.g., a chemokine such as IP-10 or Mig) or a promoter (see e.g., Taub, D. D. et al., *J. Immunol.*, 155: 3877–3888 (1995); Baggliolini, M. and C. A. Dahinden, *Immunology Today*, 15: 127–133 (1994) and references cited therein). Functions characteristic of a mammalian CXCR3 receptor may also be assessed by other suitable methods.

These methods, alone or in combination with other suitable methods can also be used in procedures for the identification and/or isolation of nucleic acids which encode a polypeptide having the amino acid sequence SEQ ID NO:2 or functional equivalents thereof, and having an activity detected by the assay. Portions of isolated nucleic acids which encode polypeptide portions of SEQ ID NO:2 having a certain function can be also identified and isolated in this manner.

Nucleic acids of the present invention can be used in the production of proteins or polypeptides. For example, a nucleic acid containing all or part of the coding sequence for a mammalian CXCR3 receptor, or DNA which hybridizes to the sequence SEQ ID NO:1, or the complement thereof, can be incorporated into a construct for further manipulation of sequences or for production of the encoded polypeptide in suitable host cells. Nucleic acids of the present invention can also be modified, for example, by incorporation of or attachment (directly or indirectly) of a detectable label such as a radioisotope, spin label, antigen or enzyme label, flourescent or chemiluminesent group and the like, and such modified forms are included within the scope of the invention.

Antisense Constructs

In another embodiment, the nucleic acid is an antisense nucleic acid, which is complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell using suitable methods, antisense nucleic acid can inhibit the expression of the gene encoded by the sense strand. Antisense nucleic acids can be produced by standard techniques.

In one embodiment, the antisense nucleic acid is wholly or partially complementary to and can hybridize with a target nucleic acid, wherein the target nucleic acid can hybridize to a nucleic acid having the sequence of the complement of SEQ ID NO:1. For example, antisense nucleic acid can be complementary to a target nucleic acid having the sequence of SEQ ID NO:1 or a portion thereof sufficient to allow hybridization. In another embodiment, the antisense nucleic acid is wholly or partially complementary to and can hybridize with a target nucleic acid which encodes a mammalian CXCR3 receptor (e.g., human IP-10/Mig receptor CXCR3).

Antisense nucleic acids are useful for a variety of purposes, including research and therapeutic applications. For example, a construct comprising an antisense nucleic acid can be introduced into a suitable cell to inhibit receptor expression. Such a cell provides a valuable control cell, for instance in assessing the specificity of receptor-ligand interaction with the parent cell or other related cell types. In another aspect, such a construct can be introduced into some or all of the cells of a mammal. The antisense nucleic acid inhibits receptor expression, and inflammatory processes mediated by CXCR3 receptors in the cells containing the construct can be inhibited. Thus, an inflammatory disease or condition can be treated using an antisense nucleic acid of the present invention. Suitable laboratory animals comprising an antisense construct can also provide useful models for deficiencies of leukocyte function, and of activated T lymphocyte deficiency in particular, and can provide further information regarding CXCR3 receptor function. Such animals can provide valuable models of infectious disease or cancer, useful for elucidating the role of leukocytes, such as T lymphocytes and NK cells, in host defenses.

Method of Producing Recombinant Proteins

Another aspect of the invention relates to a method of producing a mammalian CXCR3 protein or variant (e.g., portion) thereof. Recombinant protein can be obtained, for example, by the expression of a recombinant nucleic acid (e.g., DNA) molecule encoding a mammalian CXCR3 or variant thereof in a suitable host cell, for example.

Constructs (e.g., expression vectors) suitable for the expression of a mammalian CXCR3 protein or variant thereof are also provided. The constructs can be introduced into a suitable host cell, and cells which express a recombinant mammalian CXCR3 protein or variant thereof can be produced and maintained in culture. Such cells are useful for a variety of purposes, including use in the production of protein for characterization, isolation and/or purification, (e.g., affinity purification), use as immunogen, and in binding assays or other functional assays (e.g., to screen for ligands, inhibitors and/or promoters of receptor function), for instance. Suitable host cells can be procaryotic, including bacterial cells such as *E. coli, B. subtilis* and or other suitable bacteria, or eucaryotic, such as fungal or yeast cells (e.g., *Pichia pastoris, Aspergillus* species, *Saccharomyces cerevisiae, Schizosaccharomyces pombe, Neurospora crassa*), or other lower eucaryotic cells, and cells of higher eucaryotes such as those from insects (e.g., Sf9 insect cells (WO 94/26087, O'Connor, published Nov. 24, 1994)) or mammals (e.g., Chinese hamster ovary cells (CHO), COS cells, HuT 78 cells, 293 cells). (See, e.g., Ausubel, F. M. et al., eds. *Current Protocols in Molecular Biology*, Greene Publishing Associates and John Wiley & Sons Inc., (1993)).

Host cells which produce a recombinant mammalian CXCR3 protein or variant thereof can be produced as follows. For example, a nucleic acid encoding all or part of the coding sequence for the desired protein can be inserted into a nucleic acid vector, e.g., a DNA vector, such as a plasmid, virus or other suitable replicon for expression. A variety of vectors are available, including vectors which are maintained in single copy or multiple copy, or which become integrated into the host cell chromosome.

Transcriptional and/or translational signals of a mammalian CXCR3 gene can be used to direct expression. Suitable expression vectors for the expression of a nucleic acid encoding all or part of the coding sequence of the desired protein are also available. Suitable expression vectors can contain a number of components, including, but not limited to one or more of the following: an origin of replication; a selectable marker gene; one or more expression control elements, such as a transcriptional control element (e.g., a promoter, an enhancer, terminator), and/or one or more translation signals; a signal sequence or leader sequence for membrane targeting in a selected host cell (e.g., of mammalian origin or from a heterologous mammalian or non-mammalian species). In a construct, a signal sequence can be provided by the vector, the mammalian CXCR3 coding sequence, or other source.

A promoter can be provided for expression in a suitable host cell. Promoters can be constitutive or inducible. In the vectors, a promoter can be operably linked to a nucleic acid encoding the mammalian CXCR3 protein or variant thereof, such that it directs expression of the encoded polypeptide. A variety of suitable promoters for procaryotic (e.g., lac, tac, T3, T7 promoters for *E. coli*) and eucaryotic (e.g., yeast alcohol dehydrogenase (ADH1), SV40, CMV) hosts are available.

In addition, the expression vectors typically comprise a selectable marker for selection of host cells carrying the vector, and, in the case of replicable expression vector, an origin or replication. Genes encoding products which confer antibiotic or drug resistance are common selectable markers and may be used in procaryotic (e.g., O-lactamase gene (ampicillin resistance), Tet gene for tetracycline resistance) and eucaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated. The present invention also relates to cells carrying these expression vectors.

For example, a nucleic acid encoding a mammalian CXCR3 protein or variant thereof, or a construct comprising such nucleic acid, can be introduced into a suitable host cell by a method appropriate to the host cell selected (e.g., transformation, transfection, electroporation, infection), such that the nucleic acid is operably linked to one or more expression control elements (e.g., in a vector, in a construct created by processes in the cell, integrated into the host cell genome). Host cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded protein (e.g., human CXCR3) can be isolated (e.g., from the host cells, medium, milk). It will be appreciated that the method encompasses expression in a host cell of a transgenic animal (see e.g., WO 92/03918, GenPharm International, published Mar. 19, 1992).

Fusion proteins can also be produced in this manner. For example, some embodiments can be produced by the insertion of a mammalian CXCR3 protein cDNA or portion thereof into a suitable expression vector, such as Bluescript®II SK+/−(Stratagene), pGEX-4T-2 (Pharmacia), pcDNA-3 (Invitrogen) or pET-15b (Novagen). The resulting construct can be introduced into a suitable host cell for expression. Upon expression, fusion protein can be isolated or purified from a cell lysate by means of a suitable affinity matrix (see e.g., *Current Protocols in Molecular Biology* (Ausubel, F. M. et al., eds., Vol. 2, Suppl. 26, pp. 16.4.1–16.7.8 (1991)). In addition, affinity labels provide a means of detecting a fusion protein. For example, the cell surface expression or presence in a particular cell fraction of a fusion protein comprising an antigen or epitope affinity label can be detected by means of an appropriate antibody.

Antibodies

The invention further relates to antibodies reactive with a mammalian CXCR3 protein or portion thereof. In one embodiment, antibodies are raised against an isolated and/or recombinant mammalian CXCR3 protein or portion thereof (e.g., a peptide) or against a host cell which expresses recombinant mammalian CXCR3. In a preferred embodiment, antibodies specifically bind mammalian CXCR3 receptor(s) or a portion thereof, and in a particularly preferred embodiment the antibodies can inhibit (reduce or prevent) the interaction of receptor with a natural ligand, such as IP-10 and/or Mig.

The antibodies of the present invention can be polyclonal or monoclonal, and the term antibody is intended to encompass both polyclonal and monoclonal antibodies. The terms polyclonal and monoclonal refer to the degree of homogeneity of an antibody preparation, and are not intended to be limited to particular methods of production.

Antibodies of the present invention can be raised against an appropriate immunogen, including proteins or polypeptides of the present invention, such as isolated and/or recombinant mammalian CXCR3 protein or portion thereof (including synthetic molecules, such as synthetic peptides). In addition, cells expressing recombinant mammalian CXCR3, such as transfected cells, can be used as immunogens or in a screen for antibody which binds receptor. See for example, Chuntharapai et al., *J. Immunol.*, 152: 1783–1789 (1994); Chuntharapai et al., U.S. Pat. No. 5,440,021).

Preparation of immunizing antigen, and polyclonal and monoclonal antibody production can be performed using any suitable technique. A variety of methods have been described (see e.g., Kohler et al., *Nature*, 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0) with antibody producing cells. The antibody producing cell, preferably those of the spleen or lymph nodes, can be obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies (see e.g., Jakobovits et al., *Proc. Natl. Acad. Sci. USA,* 90: 2551–2555 (1993); Jakobovits et al., *Nature,* 362: 255–258 (1993); Lonberg et al., U.S. Pat. No. 5,545,806; Surani et al., U.S. Pat. No. 5,545,807).

Single chain antibodies, and chimeric, humanized or primatized (CDR-grafted), or veneered antibodies, as well as chimeric, CDR-grafted or veneerd single chain antibodies, comprising portions derived from different species, and the like are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., *BioTechnology,* 10: 1455–1460 (1992), regarding primatized antibody, and Ladner et al., U.S. Pat. No. 4,946,778 and Bird, R. E. et al., *Science,* 242: 423–426 (1988)) regarding single chain antibodies.

In addition, functional fragments of antibodies, including fragments of chimeric, humanized, primatized, veneered or single chain antibodies, can also be produced. Functional fragments of foregoing antibodies retain at least one binding function and/or modulation function of the full-length antibody from which they are derived. For example, antibody fragments capable of binding to a mammalian CXCR3 protein or portion thereof, including, but not limited to, Fv, Fab, Fab' and F(ab')$_2$ fragments are encompassed by the invention. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

The antibodies of the present invention are useful in a variety of applications, including research, diagnostic and therapeutic applications. For instance, they can be used to isolate and/or purify receptor or portions thereof, and to study receptor structure (e.g., conformation) and function.

The antibodies of the present invention can also be used to modulate receptor function in research and therapeutic applications. For instance, antibodies can act as inhibitors to inhibit (reduce or prevent) (a) binding (e.g., of a ligand, a second inhibitor or a promoter) to the receptor, (b) receptor signalling, and/or (c) a cellular response. Antibodies which act as inhibitors of receptor function can block ligand or promoter binding directly or indirectly (e.g., by causing a conformational change in the receptor). For example, antibodies can inhibit receptor function by inhibiting binding of a ligand, or by desensitization (with or without inhibition of binding of a ligand).

Antibodies which bind receptor can also act as agonists of receptor function, triggering or stimulating a receptor function, such as signalling and/or a cellular response (e.g., calcium flux, chemotaxis, exocytosis or pro-inflammatory mediator release) upon binding to receptor.

In addition, the various antibodies of the present invention can be used to detect or measure the expression of receptor, for example, on leukocytes such as activated T cells or natural killer cells (NK cells), or on cells transfected with a receptor gene. Thus, they also have utility in applications such as cell sorting (e.g., flow cytometry, fluorescence activated cell sorting), for diagnostic or research purposes.

Anti-idiotypic antibodies are also provided. Anti-idiotypic antibodies recognize antigenic determinants associated with the antigen-binding site of another antibody. Anti-idiotypic antibodies can be prepared a against a first antibody by immunizing an animal of the same species, and preferably of the same strain as the animal used to produce the first antibody, with said first antibody. See e.g., U.S. Pat. No. 4,699,880.

In one embodiment, antibodies are raised against receptor or a portion thereof, and these antibodies are used in turn as immunogen to produce an anti-idiotypic antibody. The anti-Id produced thereby can mimic receptor and bind compounds which bind receptor, such as ligands, inhibitors or promoters of receptor function, and can be used in an immunoassay to detect, identify or quantitate such compounds. Such an anti-idiotypic antibody can also be an inhibitor of receptor function, although it does not bind receptor itself.

Anti-idiotypic (i.e., Anti-Id) antibody can itself be used to raise an anti-idiotypic antibody (i.e., Anti-anti-Id). Such an antibody can be similar or identical in specificity to the original immunizing antibody. In one embodiment, antibody antagonists which block binding to receptor can be used to raise Anti-Id, and the Anti-Id can be used to raise Anti-anti-Id, which can have a specificity which is similar or identical to that of the antibody antagonist. These anti-anti-Id antibodies can be assessed for inhibitory effect on receptor function to determine if they are antagonists.

Single chain, and chimeric, humanized, primatized (CDR-grafted), veneered, as well as chimeric, CDR-grafted, or veneered single chain anti-idiotypic antibodies can be prepared, and are encompassed by the term anti-idiotypic antibody. Antibody fragments of such antibodies can also be prepared.

The antibodies and fragments of the present invention can be modified, for example, by incorporation of or attachment (directly or indirectly) of a detectable label such as a radioisotope, spin label, antigen or enzyme label, flourescent or chemiluminesent group and the like, and such modified forms are included within the scope of the invention.

Identification of Ligands, Inhibitors or Promoters of Receptor Function

As used herein, a ligand is a substance which binds to a receptor protein. A ligand of a selected mammalian CXCR3 protein is a substance which binds to the selected mammalian CXCR3 protein. In a preferred embodiment, ligand binding of a mammalian CXCR3 protein occurs with high affinity. The term ligand refers to substances including, but not limited to, a natural ligand, whether isolated and/or purified, synthetic, and/or recombinant, a homolog of a natural ligand (e.g., from another mammal), antibodies, portions of such molecules, and other substances which bind receptor. A natural ligand of a selected mammalian receptor can bind to the receptor under physiological conditions, and is of a mammalian origin which is the same as that of the mammalian CXCR3 protein. The term ligand encompasses substances which are inhibitors or promoters of receptor activity, as well as substances which bind receptor, but lack inhibitor or promoter activity.

As used herein, an inhibitor is a substance which inhibits at least one function characteristic of a mammalian CXCR3 protein (e.g., a human CXCR3), such as a binding activity (e.g., ligand binding, promoter binding), a signalling activity (e.g., activation of a mammalian G protein, induction of rapid and transient increase in the concentration of cytosolic free calcium $[Ca^{2+}]_i$), and/or cellular response function (e.g., stimulation of chemotaxis, exocytosis or inflammatory mediator release by leukocytes). The term inhibitor refers to substances including antagonists which bind receptor (e.g., an antibody, a mutant of a natural ligand, other competitive inhibitors of ligand binding), and substances which inhibit receptor function without binding thereto (e.g., an anti-idiotypic antibody).

As used herein, a promoter is a substance which promotes (induces or enhances) at least one function characteristic of a mammalian CXCR3 protein (e.g., a human CXCR3), such as a binding activity (e.g., ligand, inhibitor and/or promoter binding), a signalling activity (e.g., activation of a mammalian G protein, induction of rapid and transient increase in the concentration of cytosolic free calcium $[Ca^{2+}]_i$), and/or a cellular response function (e.g., stimulation of chemotaxis, exocytosis or inflammatory mediator release by leukocytes). The term promoter refers to substances including agonists which bind receptor (e.g., an antibody, a homolog of a natural ligand from another species), and substances which promote receptor function without binding thereto (e.g., by activating an associated protein). In a preferred embodiment, the agonist is other than a homolog of a natural ligand.

The assays described below, which rely upon the nucleic acids and proteins of the present invention, can be used, alone or in combination with each other or other suitable methods, to identify ligands, inhibitors or promoters of a mammalian CXCR3 protein or variant. The in vitro methods of the present invention can be adapted for high-throughput screening in which large numbers of samples are processed (e.g., a 96 well format). Host cells comprising a nucleic acid of the present invention and expressing recombinant mammalian CXCR3 (e.g., human CXCR3) at levels suitable for high-throughput screening can be used, and thus, are particularly valuable in the identification and/or isolation of ligands, inhibitors and promoters of mammalian CXCR3 proteins. Expression of receptor can be monitored in a variety of ways. For instance, expression can be monitored using antibodies of the present invention which bind receptor or a portion thereof. Also, commercially available antibodies can be used to detect expression of an antigen- or epitope-tagged fusion protein comprising a receptor protein or polypeptide (e.g., FLAG tagged receptors), and cells expressing the desired level can be selected.

Nucleic acid encoding a mammalian CXCR3 protein, the can be incorporated into an expression system to produce a receptor protein or polypeptide as described above. An isolated and/or recombinant receptor protein or polypeptide, such as a receptor expressed in cells stably or transiently transfected with a construct comprising a nucleic acid of the present invention, or in a cell fraction containing receptor (e.g., a membrane fraction from transfected cells, liposomes incorporating receptor), can be used in tests for receptor function. The receptor can be further purified if desired. Testing of receptor function can be carried out in vitro or in vivo.

An isolated, recombinant mammalian CXCR3 protein, such as a human CXCR3 as shown in FIG. 2 (SEQ ID NO:2), can be used in the present method, in which the effect of a compound is assessed by monitoring receptor function as described herein or using other suitable techniques. For example, stable or transient transfectants such as those described in Example 2 or other suitable cells (e.g., baculovirus infected Sf9 cells, stable tranfectants of mouse L1-2 pre-B cells (derived from a pre-B lymphoma, Dr. Eugene Butcher (Stanford University, Stanford, Calif.)), can be used in binding assays. Stable transfectants of Jurkat cells (Example 2) or of other suitable cells capable of chemotaxis can be used (e.g., mouse L1-2 pre-B cells) in chemotaxis assays, for example.

According to the method of the present invention, compounds can be individually screened or one or more compounds can be tested simultaneously according to the methods herein. Where a mixture of compounds is tested, the compounds selected by the processes described can be separated (as appropriate) and identified by suitable methods (e.g., PCR, sequencing, chromatography). The presence of one or more compounds (e.g., a ligand, inhibitor, promoter) in a test sample can also be determined according to these methods.

Large combinatorial libraries of compounds (e.g., organic compounds, recombinant or synthetic peptides, "peptoids", nucleic acids) produced by combinatorial chemical synthesis or other methods can be tested (see e.g., Zuckerman, R. N. et al., *J. Med. Chem.*, 37: 2678–2685 (1994) and references cited therein; see also, Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible.

In one embodiment, phage display methodology is used. For example, receptor can be contacted with a phage (e.g., a phage or collection of phage such as a library) displaying a polypeptide under conditions appropriate for receptor binding (e.g., in a suitable binding buffer). Phage bound to receptor can be selected using standard techniques or other suitable methods. Phage can be separated from receptor using a suitable elution buffer. For example, a change in the ionic strength or pH can lead to a release of phage. Alternatively, the elution buffer can comprise a release component or components designed to disrupt binding of compounds (e.g., one or more compounds which can disrupt binding of the displayed peptide to the receptor, such as a ligand, inhibitor, and/or promoter which competitively inhibits binding). Optionally, the selection process can be repeated or another selection step can be used to further enrich for phage which bind receptor. The displayed polypeptide can be characterized (e.g., by sequencing phage DNA). The polypeptides identified can be produced and further tested for ligand binding, inhibitor and/or promoter function. Analogs of such peptides can be produced which will have increased stability or other desirable properties.

In one embodiment, phage expressing and displaying fusion proteins comprising a coat protein with an N-terminal peptide encoded by random sequence nucleic acids can be produced. Suitable host cells expressing a receptor protein or polypeptide of the present invention are contacted with the phage, bound phage are selected, recovered and characterized. (See e.g., Doorbar, J. and G. Winter, *J. Mol. Biol.*, 244: 361 (1994) discussing a phage display procedure used with a G protein-coupled receptor).

Other sources of potential ligands, inhibitors and/or promoters of mammalian CXCR3 proteins include, but are not limited to, variants of CXCR3 ligands, including naturally occurring, synthetic or recombinant variants of IP-10 or Mig, substances such as other chemoattractants or chemokines, variants thereof, other inhibitors and/or promoters (e.g., anti-CXCR3 antibodies, antagonists, agonists), other G-protein coupled receptor ligands, inhibitors and/or promoters (e.g., antagonists or agonists), and soluble portions of a mammalian CXCR3 receptor, such as a suitable receptor peptide or analog which can inhibit receptor function (see e.g., Murphy, R. B., WO 94/05695).

Binding Assays

The isolated and/or recombinant receptor proteins, portions thereof, or suitable fusion proteins of the present invention, can be used in a method to select and identify agents which bind to a (one or more) mammalian CXCR3 protein, such as human CXCR3, and which are ligands, or potential inhibitors or promoters of receptor activity. Agents selected by the method, including ligands, inhibitors or promoters, can be further assessed for an inhibitory or stimulatory effect on receptor function and/or for therapeutic utility.

In one embodiment, an agent which binds to an active, isolated and/or recombinant mammalian CXCR3 protein or polypeptide is identified by the method. In this embodiment, the receptor protein or polypeptide used has at least one property, activity or function characteristic of a mammalian CXCR3 protein (as defined herein), such as a binding activity (e.g., ligand, inhibitor and/or promoter binding), a signalling activity (e.g., activation of a mammalian G protein, induction of rapid and transient increase in the concentration of cytosolic free calcium $[Ca^{2+}]_i$), cellular response function (e.g., stimulation of chemotaxis, exocytosis or inflammatory mediator release by leukocytes), and/or an immunological property as defined herein. In a preferred embodiment, the isolated and/or recombinant mammalian CXCR3 protein or variant has ligand binding function, and more preferably binds a natural ligand of the receptor. In a particularly preferred embodiment, the isolated and/or recombinant protein is a human CXCR3 protein encoded by the nucleic acid illustrated FIG. 1 (SEQ ID NO:1).

For example, a composition comprising an isolated and/or recombinant mammalian CXCR3 protein or variant thereof can be maintained under conditions suitable for binding, the receptor can be contacted with an agent (e.g., a composition comprising one or more agent) to be tested, and binding is detected or measured. In one embodiment, a receptor protein can be expressed in cells stably or transiently transfected with a construct comprising a nucleic acid sequence which encodes a receptor of the present invention. The cells can be maintained under conditions appropriate for expression of receptor. The cells are contacted with an agent under conditions suitable for binding (e.g., in a suitable binding buffer), and binding can be detected by standard techniques. For example, the extent of binding can be determined relative to a suitable control (e.g., compared with background determined in the absence of agent, compared with binding of a second agent (i.e., a standard), compared with binding of the agent to untransfected cells). Optionally, a cellular fraction, such as a membrane fraction, containing receptor can be used in lieu of whole cells.

Binding or complex formation can be detected directly or indirectly. In one embodiment, the agent can be labeled with a suitable label (e.g., fluorescent label, chemiluminescent label, isotope label, enzyme label), and binding can be determined by detection of the label. Specificity of binding can be assessed by competition or displacement, for example, using unlabeled agent or a ligand (e.g., IP-10, Mig) as competitor.

Ligands of the mammalian receptor, including natural ligands from the same mammalian species or from another species, can be identified in this manner. The binding activity of a promoter or inhibitor which binds receptor can also be assessed using such a ligand binding assay.

Binding inhibition assays can also be used to identify ligands, and inhibitors and promoters which bind receptor and inhibit binding of another agent such as a ligand. For example, a binding assay can be conducted in which a reduction in the binding of a first agent (in the absence of a second agent), as compared with binding of the first agent in the presence of the second test agent, is detected or measured. The receptor can be contacted with the first and second agents simultaneously, or one after the other, in either order. A reduction in the extent of binding of the first agent in the presence of the second test agent, is indicative of inhibition of binding by the second agent. For example, binding of the first agent could be decreased or abolished.

In one embodiment, direct inhibition of the binding of a first agent (e.g., a chemokine such as IP-10, Mig) to a human CXCR3 by a second test agent is monitored. For example, the ability of an agent to inhibit the binding of $^{125}$I-labeled Mig to human CXCR3 can be monitored. Such an assay can be conducted using whole cells (e.g., a suitable cell line containing nucleic acid encoding a human CXCR3 receptor), or a membrane fraction from said cells, for instance.

Other methods of identifying the presence of an agent(s) which binds a receptor are available, such as methods which monitor events which are triggered by receptor binding, including signalling function and/or stimulation of a cellular response.

It will be understood that the inhibitory effect of antibodies of the present invention can be assessed in a binding inhibition assay. Competition between antibodies for receptor binding can also be assessed in the method in which the first agent in the assay is another antibody, under conditions suitable for antibody binding.

Ligands, receptor-binding inhibitors and promoters, which are identified in this manner, can be further assessed to determine whether, subsequent to binding, they act to inhibit or activate other functions of CXCR3 receptors and/or to assess their therapeutic utility.

Signalling Assays

The binding of a G protein-coupled receptor (e.g., by an agonist) can result in signalling by the receptor, and stimulation of the activity of G protein. The induction of signalling function by an agent can be monitored using any suitable method. For example, G protein activity, such as hydrolysis of GTP to GDP, or later signalling events triggered by receptor binding, such as induction of rapid and transient increase in the concentration of intracellular (cytosolic) free calcium $[Ca^{2+}]_i$, can be assayed by methods known in the art or other suitable methods (Example 2; see also, Neote, K. et al., *Cell*, 72: 415–425 1993); Van Riper et al., *J. Exp. Med.*, 177: 851–856 (1993); Dahinden, C. A. et al., *J. Exp. Med.*, 179: 751–756 (1994)).

The functional assay of Sledziewski et al. using hybrid G protein coupled receptors can also be used to identify a ligand or promoter by its ability to activate a hybrid G protein or to identify an inhibitor by its ability to inhibit such activation (Sledziewski et al., U.S. Pat. No. 5,284,746, the teachings of which are incorporated herein by reference). In one embodiment, a biological response of the host cell (triggered by binding to hybrid receptor) can be monitored, detection of the response being indicative of the presence of ligand in the test sample. For example, a method of detecting the presence of a ligand in a test sample is described, wherein the ligand is an agent which is capable of being bound by the ligand-binding domain of a receptor. In one embodiment of the method, yeast host cells are transformed with a DNA construct capable of directing the expression of a biologically active hybrid G protein-coupled receptor (i.e., a fusion protein). The hybrid receptor comprises a mammalian G protein-coupled receptor having at least one domain other than the ligand-binding domain replaced with a corresponding domain of a yeast G protein-coupled receptor, such as a STE2 gene product. The yeast host cells containing the construct are maintained under conditions in which the hybrid receptor is expressed, and the cells are contacted with a test sample under conditions suitable to permit binding of ligand to the hybrid receptor. A biological response of the host cell (triggered by binding to hybrid receptor) is monitored, detection of the response being indicative of a signalling function. For instance, binding to a hybrid receptor derived from STE2 gene product can lead to induction of the BAR1 promoter. Induction of the promoter can be measured by means of a reporter gene (e.g., β-gal), which is linked to the BAR1 promoter and introduced into host cells on a second construct. Expression of the reporter gene can be detected by an in vitro enzyme assay on cell lysates or by the presence of blue colonies on plates containing an indicator (e.g., X-gal) in the medium, for example.

In another embodiment, the assay can be used to identify potential inhibitors of receptor function. The inhibitory activity of an agent can be determined using a ligand or promoter in the assay, and assessing the ability of the test agent to inhibit the activity induced by ligand or promoter.

Variants of known ligands can also be screened for reduced ability (decreased ability or no ability) to stimulate activity of a coupled G protein. In this embodiment, although the agent has ligand binding activity (as determined by another method), engagement of the receptor does not trigger or only weakly triggers activity of a coupled G protein. Such agents are potential antagonists, and can be further assessed for inhibitory activity.

Chemotaxis and Other Assays of Cellular Responses

Chemotaxis assays can also be used to assess receptor function. These assays are based on the functional migration of cells in vitro or in viva induced by an agent, and can be used to assess the binding and/or effect on chemotaxis of ligands, inhibitors, or promoters.

The use of an in vitro chemotaxis assay to assess the response of cells to IP-10 and Mig is described in Example 2. Springer et al. describe a transendothelial lymphocyte chemotaxis assay (Springer et al., WO 94/20142, published Sep. 15, 1994, the teachings of which are incorporated herein by reference; see also Berman et al., *Immunol Invest.*, 17: 625–677 (1988)). Migration across endothelium into collagen gels has also been described (Kavanaugh et al., *J. Immunol*, 146: 4149–4156 (1991)).

Generally, chemotaxis assays monitor the directional movement or migration of a suitable cell capable of chemotaxis, such as a leukocyte (e.g., T lymphocytes, NK cells, monocytes), stable transfectants of Jurkat cells, mouse L1-2 pre-B cells or of other suitable host cells, for example, into or through a barrier (e.g., endothelium, a filter), toward increased levels of an agent, from a first surface of the barrier toward an opposite second surface. Membranes or filters provide convenient barriers, such that the directional movement or migration of a suitable cell into or through a filter, toward increased levels of an agent, from a first surface of the filter toward an opposite second surface of the filter, is monitored. In some assays, the membrane is coated with a substance to facilitate adhesion, such as ICAM-1, fibronectin or collagen.

For example, one can detect or measure the migration of cells in a suitable container (a containing means), from a first chamber into or through a microporous membrane into a second chamber which contains an agent to be tested, and which is divided from the first chamber by the membrane. A suitable membrane, having a suitable pore size for monitoring specific migration in response to the agent, including, for example, nitrocellulose, polycarbonate, is selected. For example, pore sizes of about 3–8 microns, and preferably about 5–8 microns can be used. Pore size can be uniform on a filter or within a range of suitable pore sizes.

To assess migration, the distance of migration into the filter, the number of cells crossing the filter that remain adherent to the second surface of the filter, and/or the number of cells that accumulate in the second chamber can be determined using standard techniques (e.g., by microscopy). In one embodiment, the cells are labeled with a detectable label (e.g., radioisotope, fluorescent label, antigen or epitope label), and migration can be assessed by determining the presence of the label adherent to the membrane and/or present in the second chamber using an appropriate method (e.g., by detecting radioactivity, fluorescence, immunoassay). The extent of migration induced by an agent can be determined relative to a suitable control (e.g., compared to background migration determined in the absence of the agent, to the extent of migration induced by a second agent (i.e., a standard), compared with migration of untransfected cells induced by the agent).

Chambers can be formed from various solids, such as plastic, glass, polypropylene, polystyrene, etc. Membranes which are detachable from the chambers, such as a Biocoat (Collaborative Biomedical Products) or Transwell (Costar, Cambridge, Mass.) culture insert, facilitate counting adherent cells. In the container, the filter can be situated so as to be in contact with fluid containing cells in the first chamber, and the fluid in the second chamber. Other than the test agent or additional ligand, inhibitor, or promoter present for the purpose of the assay, the fluid on either side of the membrane is preferably the same or substantially similar. The fluid in the chambers can comprise protein solutions (e.g., bovine serum albumin, fetal calf serum, human serum albumin) which may act to increase stability and inhibit nonspecific binding of cells, and/or culture media.

In one embodiment, transendothelial migration is assessed. In addition to lower background (signal to noise ratio), transendothelial migration models in vivo conditions in which leukocytes emigrate from blood vessels toward chemoattractants present in the tissues at sites of inflammation by crossing the endothelial cell layer lining the vessel wall. In this embodiment, transmigration through an endothelial cell layer assessed. To prepare the cell layer, endothelial cells can be cultured on a microporous filter or membrane, optionally coated with a substance such as collagen, fibronectin, or other extracellular matrix proteins, to facilitate the attachment of endothelial cells. Preferably, endothelial cells are cultured until a confluent monolayer is formed. A variety of mammalian endothelial cells can are available for monolayer formation, including for example, vein, artery or microvascular endothelium, such as human umbilical vein endothelial cells (Clonetics Corp, San Diego, Calif.) or a suitable cell line, such as the ECV 304 cell line used (European Collection of Animal Cell Cultures, Porton Down, Salisbury, U. K.). To assay chemotaxis in response to a particular mammalian receptor, endothelial cells of the same mammal are preferred; however endothelial cells from a heterologous mammalian species or genus can also be used.

Generally, the assay is performed by detecting the directional migration of cells into or through a membrane or filter, in a direction toward increased levels of an agent, from a first surface of the filter toward an opposite second surface of the filter, wherein the filter contains an endothelial cell layer on a first surface. Directional migration occurs from the area adjacent to the first surface, into or through the membrane, towards an agent situated on the opposite side of the filter. The concentration of agent present in the area adjacent to the second surface, is greater than that in the area adjacent to the first surface.

In one embodiment, a chemotaxis assay is used to test for ligand or promoter activity of an agent, a composition comprising cells capable of migration and expressing a mammalian CXCR3 protein are placed in the first chamber, and a composition comprising the agent (one or more agents) to be tested is placed in the second chamber, preferably in the absence of other ligands or promoters capable of inducing chemotaxis of the cells in the first chamber (having chemoattractant function). However, one or more ligands or promoters having chemoattractant function may be present. The ability of an agent to induce chemotaxis of the cells expressing a mammalian CXCR3 receptor in this assay is indicative that the agent is a ligand or promoter of receptor function.

In one embodiment used to test for an inhibitor, a composition comprising cells capable of migration and expressing a mammalian CXCR3 protein are placed in the first chamber. A composition comprising a ligand or promoter (i.e., one or more ligands or promoters) capable of inducing chemotaxis of the cells in the first chamber (having chemoattractant function) is placed in the second chamber. Before (preferably shortly before) the cells are placed in the first chamber, or simultaneously with the cells, a composition comprising the agent to be tested is placed, preferably, in the first chamber. The ability of an agent to inhibit ligand- or promoter-induced chemotaxis of the cells expressing a mammalian CXCR3 protein in this assay is indicative that the agent is an inhibitor of receptor function (e.g., an inhibitor of cellular response function). A reduction in the extent of migration induced by the ligand or promoter in the presence of the test agent, is indicative of inhibitory activity. Separate binding studies (see above) can be performed to determine whether inhibition is a result of binding of the test agent to receptor or occurs via a different mechanism.

In vivo assays which monitor leukocyte infiltration of a tissue, in response to injection of an agent in the tissue, are described below. These models measure the ability of cells to respond to a ligand or promoter by emigration and chemotaxis to a site of inflammation.

The effects of a ligand, inhibitor or promoter on the cellular response function of a CXCR3 receptor can be assessed by monitoring other cellular responses induced by active receptor, using suitable host cells containing receptor. Similarly, these assays can be used to determine the function of a receptor. For instance, exocytosis (e.g., degranulation of natural killer cells leading to release of one or more enzymes or other granule components, such as esterases (e.g., serine esterases), perforin, and/or granzymes), inflammatory mediator release (such as release of bioactive lipids such as leukotrienes (e.g., leukotriene $C_4$)), and respiratory burst, can be monitored by methods known in the art or other suitable methods. (See e.g., Taub, D. D. et al., *J. Immunol.*, 155: 3877–3888 (1995) regarding assays for release of granule-derived serine esterases (the teachings of which are incorporated herein by reference) and Loetscher et al., *J. Immunol.*, 156: 3229–327 (1996) regarding assays for enzyme and granzyme release by NK cells and cytotoxic T lymphocytes (CTLs) (the teachings of which are incorporated herein by reference); Rot, A. et al., *J. Exp. Med.*, 176: 1489–1495 (1992) regarding respiratory burst; Bischoff. S. C. et al., *Eur. J. Immunol.*, 23: 761–767 (1993) and Baggliolini, M. and C. A. Dahinden, *Immunology Today*, 15: 127–133 (1994)).

In one embodiment, a ligand, inhibitor and/or promoter is identified by monitoring the release of an enzyme upon degranulation or exocytosis by a cell capable of this function. Cells containing a nucleic acid of the present invention, which encodes an active receptor protein capable of stimulating exocytosis or degranulation are maintained in a suitable medium under suitable conditions, whereby receptor is expressed and degranulation can be induced. The receptor is contacted with an agent to be tested, and enzyme release is assessed. The release of an enzyme into the medium can be detected or measured using a suitable assay, such as in an immunological assay, or biochemical assay for enzyme activity.

The medium can be assayed directly, by introducing components of the assay (e.g., substrate, co-factors, antibody) into the medium (e.g., before, simultaneous with or after the cells and agent are combined). Alternatively, the assay can be performed on medium which has been separated from the cells or further processed (e.g., fractionated) prior to assay. For example, convenient assays for are available for enzymes such serine esterases (see e.g., Taub, D. D. et al., *J. Immunol.*, 155: 3877–3888 (1995) regarding release of granule-derived serine esterases).

Stimulation of degranulation by an agent can be indicative that the agent is a ligand or promoter of a mammalian CXCR3 protein. In another embodiment, cells expressing receptor are combined with a ligand or promoter, and an agent to be tested is added before, after or simultaneous therewith, and degranulation is assessed. Inhibition of ligand- or promoter-induced degranulation is indicative that the agent is an inhibitor of mammalian CXCR3 protein function.

Cellular adherence can also monitored by methods known in the art or other suitable methods. Engagement of the chemokine receptors of a lymphocyte can cause integrin activation, and induction of adherence to adhesion molecules expressed in vasculature or the perivascular space. In one embodiment, a ligand, inhibitor and/or promoter is identified by monitoring cellular adherence by a cell capable of adhesion. For example, an agent to be tested can be combined with (a) cells expressing receptor (preferably non-adherent cells which when transfected with receptor aquire adhesive ability), (b) a composition comprising a suitable adhesion molecule (e.g., a substrate such as a culture well coated with an adhesion molecule, such as fibronectin), and (c) a ligand or promoter (e.g., agonist), and maintained under conditions suitable for ligand- or promoter-induced adhesion. Labeling of cells with a fluorescent dye provides a convenient means of detecting adherent cells. Nonadherent cells can be removed (e.g., by washing) and the number of adherent cells determined. The effect of the agent in inhibiting or enhancing ligand- or promoter-induced adhesion can be indicative of inhibitor or promoter activity, respectively. Agents active in the assay include inhibitors and promoters of binding, signalling, and/or cellular responses. In another embodiment, an agent to be tested can be combined with cells expressing receptor and a composition comprising a suitable adhesion molecule under conditions suitable for ligand- or promoter-induced adhesion, and adhesion is monitored. Increased adhesion relative to a suitable control is indicative of the presence of a ligand and/or promoter.

Models of Inflammation

A variety of in vivo models of inflammation are available, which can be used to assess the effects of ligands, inhibitors, or promoters in vivo as therapeutic agents, including a sheep model for asthma (see e.g., Weg, V. B. et al., *J. Exp. Med.*, 177: 561 (1993), the teachings of which are incorporated herein by reference), a rat delayed type hypersensitivity model (Rand, M. L. et al., *Am. J. Pathol.*, 148: 855–864 (1996), the teachings of which are incorporated herein by reference), or other suitable models.

In addition, leukocyte infiltration upon intradermal injection of a compound into a suitable animal, such as rabbit, rat, or guinea pig, can be monitored (see e.g., Van Damme J. et al., *J. Exp. Med.*, 176: 59–65 (1992); Zachariae, C. O. C. et al., *J. Exp. Med.*, 171: 2177–2182 (1990); Jose, P. J. et al., *J. Exp. Med.*, 179: 881–887 (1994)). In one embodiment, skin biopsies are assessed histologically for infiltration of leukocytes (e.g., T lymphocytes, monocytes, natural killer cells). In another embodiment, labeled cells (e.g., cells expressing a mammalian CXCR3 protein which are labeled with $^{111}$In, for example) capable of chemotaxis and extravasation are administered to the animal. Infiltration of labelled cells in the vicinity of the site of injection of a test sample (e.g., a compound to be tested in a suitable buffer or physiological carrier) is indicative of the presence of a ligand or promoter, such as an agonist, in the sample. These assays can also be modified to identify inhibitors of chemotaxis and leukocyte extravasation. For example, an inhibitor can be administered, either before, simultaneously with or after ligand or agonist is administered to the test animal. A decrease of the extent of infiltration in the presence of inhibitor as compared with the extent of infiltration in the absence of inhibitor is indicative of inhibition.

Diagnostic Applications

The present invention has a variety of diagnostic applications. For example, a mutation(s) in a gene encoding a mammalian CXCR3 protein can cause a defect in at least one function of the encoded receptor, thereby reducing or enhancing receptor function. For instance, a mutation which produces a variant of receptor or alters the level of expression, can reduce or enhance receptor function, reducing or enhancing processes mediated by receptor (e.g., inflammatory processes). The presence of such a mutation can be determined using methods which detect or measure the presence of receptor or receptor function in cells (e.g., leukocytes, such as activated T lymphocytes) of an individual or in a receptor preparation isolated from such cells. In these assays, reduced or enhanced levels of receptor and/or reduced or enhanced receptor function can be assessed.

The nucleic acids of the present invention provide reagents, such as probes and PCR primers, which can be used to screen for, characterize and/or isolate a defective mammalian CXCR3 gene, which encodes a receptor having reduced or enhanced activity. Standard methods of screening for a defective gene can be employed, for instance. A defective gene can be isolated and expressed in a suitable host cell for further assessment as described herein for mammalian CXCR3 proteins. A number of human diseases are associated with defects in the function of a G-protein coupled receptor (Clapham, D. E., *Cell,* 75: 1237–1239 (1993); Lefkowitz, R. J., *Nature,* 365: 603–04 (1993)).

The nucleic acids of the present invention provide reagents, such as probes and PCR primers, which can also be used to assess expression of receptor (e.g., by detecting transcription of mRNA) by cells in a sample (e.g., by Northern analysis, by in situ hybridization). For example, expression in activated T lymphocytes or other cell types can be assessed.

The antibodies of the present invention have application in procedures in which receptor can be detected on the surface of cells. The receptor provides a marker of the leukocyte cell types in which it is expressed, particularly of activated T cells. For example, antibodies raised against a receptor protein or peptide can be used to detect and/or quantify cells expressing receptor. In one embodiment, the antibodies can be used to sort cells which express receptor from among a mixture of cells (e.g., to isolate activated T cells, such as $CD4^+$ T cells). Suitable methods for counting and/or sorting cells can be used for this purpose (e.g., flow cytometry, fluorescence activated cell sorting). Cell counts can be used in the diagnosis of diseases or conditions in which an increase or decrease in leukocyte cell types (e.g., activated T cells) is observed. The presence of an increased level of activated T cells in a sample obtained from an individual can be indicative of infiltration due to an inflammatory disease or condition, such as a delayed type hypersensitivity reaction, allograft rejection, or a pathologic condition, including bacterial or viral infection.

Furthermore, the antibodies can be used to detect or measure expression of receptor. For example, antibodies of the present invention can be used to detect or measure receptor in a sample (e.g., tissues or body fluids from an individual such as blood, serum, leukocytes (e.g., activated T lymphocytes), bronchoalveolar lavage fluid, saliva, bowel fluid). For example, a sample (e.g., tissue and/or fluid) can be obtained from an individual and a suitable assay can be used to assess the presence or amount of CXCR3 protein. Suitable assays include immunological methods such as FACS analysis and enzyme-linked immunosorbent assays (ELISA), including chemiluminescence assays, radioimmunoassay, and immunohistology. Generally, a sample and antibody of the present invention are combined under conditions suitable for the formation of an antibody-receptor complex, and the formation of antibody-receptor complex is assessed (directly or indirectly).

The presence of an increased level of receptor reactivity in a sample obtained from an individual can be indicative of inflammation and/or leukocyte (e.g., activated T cell) infiltration and/or accumulation associated with an inflammatory disease or condition, such as allograft rejection, delayed type hypersensitivity reaction, or an infection such as a viral or bacterial infection. The level of expression of a mammalian CXCR3 protein or variant can also be used to correlate increased or decreased expression of a mammalian CXCR3 protein with a particular disease or condition, and in the diagnosis of a disease or condition in which increased or decreased expression of a mammalian CXCR3 protein occurs (e.g., increased or decreased relative to a suitable control, such as the level of expression in a normal individual).

Transgenic Animals

Transgenic animals, in which the genome of the animal host is altered using recombinant DNA techniques, can be constructed. In one embodiment, the alteration is not heritable (e.g., somatic cells, such as progenitor cells in bone marrow, are altered). In another embodiment, the alteration is heritable (the germ line is altered). Transgenic animals can be constructed using standard techniques or other suitable methods (see e.g., Cooke. M. P. et al., *Cell,* 65: 281–291 (1991) regarding alteration of T lymphocytes; Hanahan, D., *Science,* 246: 1265–1275, (1989); Anderson et al., U.S. Pat. No. 5,399,346).

In one aspect, an endogenous mammalian CXCR3 gene can be inactivated or disabled, in whole or in part, in a suitable animal host (e.g., by gene disruption techniques) to produce a transgenic animal. Nucleic acids of the present invention can be used to assess successful construction of a host containing an inactivated or disabled CXCR3 gene (e.g., by Southern hybridization). In addition, successful construction of a host containing an inactivated or disabled CXCR3 gene can be assessed by suitable assays which monitor the function of the encoded receptor. Such animals can be used to assess the effect of receptor inactivation on inflammation and host defenses against cancer and pathogens (e.g., a viral pathogen).

In another embodiment, a nucleic acid encoding a mammalian CXCR3 protein or polypeptide is introduced into a suitable host to produce a transgenic animal. In a preferred embodiment, endogenous CXCR3 receptor genes present in the transgenic animals are inactivated (e.g., simultaneously with introduction of the nucleic acid by homologous recombination, which disrupts and replaces the endogenous gene). For example, a transgenic animal (e.g., a mouse, guinea pig, sheep) capable of expressing a nucleic acid encoding a mammalian CXCR3 receptor of a different mammalian species (e.g., a human CXCR3 such as the CXCR3 encoded by SEQ ID NO:1) in leukocytes (such as lymphocytes (e.g., activated T lymphocytes), natural killer cells) can be produced, and provides a convenient animal model for assessing the function of the introduced receptor. In addition, a test agent can be administered to the transgenic animal, and the effect of the agent on a receptor-mediated process (e.g., inflammation) can be monitored as described herein or using other suitable assays. In this manner, agents which inhibit or promote receptor function can be identified or assessed for in vivo effect.

Methods of Therapy

Modulation of mammalian CXCR3 function according to the present invention, through the inhibition or promotion of at least one function characteristic of a mammalian CXCR3 protein, provides an effective and selective way of inhibiting or promoting receptor-mediated functions. As CXC chemokine receptors selectively expressed on activated lymphocytes, responsive to chemokines such as IP-10 and Mig whose primary targets are lymphocytes, particularly effector cells such as activated or stimulated T lymphocytes and NK cells, mammalian CXCR3 proteins provide a target for selectively interfering with or promoting lymphocyte function in a mammal, such as a human. Once lymphocytes are recruited to a site, other leukocyte types, such as monocytes, may be recruited by secondary signals. Thus, agents which inhibit or promote CXCR3 function, including ligands, inhibitors and/or promoters, such as those identified as described herein, can be used to modulate leukocyte function (e.g., leukocyte infiltration including recruitment and/or accumulation), particularly of lymphocytes, for therapeutic purposes.

In one aspect, the present invention provides a method of inhibiting or promoting an inflammatory response in an individual in need of such therapy, comprising administering an agent which inhibits or promotes mammalian CXCR3 function to an individual in need of such therapy. In one embodiment, a compound which inhibits one or more functions of a mammalian CXCR3 protein (e.g., a human CXCR3) is administered to inhibit (i.e., reduce or prevent) inflammation. As a result, one or more inflammatory processes, such as leukocyte emigration, chemotaxis, exocytosis (e.g., of enzymes) or inflammatory mediator release, is inhibited. For example, leukocytic infiltration of inflammatory sites (e.g., in a delayed-type hypersensitivity response) can be inhibited according to the present method.

In another embodiment, an agent (e.g., receptor agonist) which promotes one or more functions of a mammalian CXCR3 protein (e.g., a human CXCR3) is administered to induce (trigger or enhance) an inflammatory response, such as leukocyte emigration, chemotaxis, exocytosis (e.g., of enzymes) or inflammatory mediator release, resulting in the beneficial stimulation of inflammatory processes. For example, natural killer cells can be recruited to combat viral infections or neoplastic disease.

The term "individual" is defined herein to include animals such as mammals, including, but not limited to, primates (e.g., humans), cows, sheep, goats, horses, dogs, cats, rabbits, guinea pigs, rats, mice or other bovine, ovine, equine, canine, feline, rodent or murine species. Diseases and conditions associated with inflammation, infection, and cancer can be treated using the method. In a preferred embodiment, the disease or condition is one in which the actions of lymphocytes, particularly effector cells such as activated or stimulated T lymphocytes and natural killer (NK) cells, are to be inhibited or promoted for therapeutic (including prophylactic) purposes. In a particularly preferred embodiment, the inflammatory disease or condition is a T cell-mediated disease or condition.

Diseases or conditions, including chronic diseases, of humans or other species which can be treated with inhibitors of CXCR3 function, include, but are not limited to:

inflammatory or allergic diseases and conditions, including systemic anaphylaxis or hypersensitivity responses, drug allergies (e.g., to penicillin, cephalosporins), insect sting allergies; inflammatory bowel diseases, such as Crohn's disease, ulcerative colitis, and ileitis; psoriasis and inflammatory dermatoses such as dermatitis, eczema, atopic dermatitis, allergic contact dermatitis, urticaria; vasculitis (e.g., necrotizing, cutaneous, and hypersensitivity vasculitis); spondyloarthropathies; scleroderma; respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, or other autoimmune conditions);

autoimmune diseases, such as arthritis (e.g., rheumatoid arthritis, psoriatic arthritis), multiple sclerosis, systemic lupus erythematosus, myasthenia gravis, juvenile onset diabetes, glomerulonephritis, autoimmune thyroiditis, Behcet's disease;

graft rejection (e.g., in transplantation), including allograft rejection or graft-versus-host disease;

other diseases or conditions in which undesirable inflammatory responses are to be inhibited can be treated, including, but not limited to, atherosclerosis, cytokine-induced toxicity, myositis (including polymyositis, dermatomyositis).

Diseases or conditions of humans or other species which can be treated with promoters (e.g., an agonist) of CXCR3 function, include, but are not limited to:

cancers, particularly those with leukocytic infiltration of the skin or organs such as cutaneous T cell lymphoma (e.g., mycosis fungoides);

diseases in which angiogenesis or neovascularization plays a role, including neoplastic disease, and retinopathy (e.g., diabetic retinopathy), macular degeneration;

infectious diseases, such as bacterial infections and tuberculoid leprosy, and especially viral infections;

immunosuppression, such as that in individuals with immunodeficiency syndromes such as AIDS, individuals undergoing radiation therapy, chemotherapy, or other therapy which causes immunosuppression; immunosuppression due congenital deficiency in receptor function or other causes. Promoters of CXR4 function can also have protective effects useful to combat stem cell depletion during cancer chemotherapy (Sarris, A. H. et al., *J. Exp. Med.*, 178: 1127–1132 (1993)).

Modes of Administration

According to the method, one or more agents can be administered to the host by an appropriate route, either alone or in combination with another drug. An effective amount of an agent (e.g., a receptor peptide which inhibits ligand binding, an anti-CXCR3 antibody or antigen-binding fragment thereof) is administered. An effective amount is an amount sufficient to achieve the desired therapeutic or prophylactic effect, under the conditions of administration, such as an amount sufficient for inhibition or promotion of CXCR3 receptor function, and thereby, inhibition or promotion, respectively, of a receptor-mediated process (e.g., an inflammatory response).

A variety of routes of administration are possible including, but not necessarily limited to oral, dietary, topical, parenteral (e.g., intravenous, intraarterial, intramuscular, subcutaneous injection), and inhalation (e.g., intrabronchial, intranasal or oral inhalation, intranasal drops) routes of administration, depending on the agent and disease or condition to be treated. For respiratory allergic diseases such as asthma, inhalation is a preferred mode of administration.

Formulation of an agent to be administered will vary according to the route of administration selected (e.g., solution, emulsion, capsule). An appropriate composition comprising the agent to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils, for instance. Intravenous vehicles can include various additives, preservatives, or fluid, nutrient or electrolyte replenishers and the like (See, generally, *Remington's Pharmaceutical Sciences,* 17th Edition, Mack Publishing Co., PA, 1985). For inhalation, the agent can be solubilized and loaded into a suitable dispenser for administration (e.g., an atomizer, nebulizer or pressurized aerosol dispenser).

Furthermore, where the agent is a protein or peptide, the agent can be administered via in vivo expression of the recombinant protein. In vivo expression can be accomplished via somatic cell expression according to suitable methods (see, e.g. U.S. Pat. No. 5,399,346). In this embodiment, nucleic acid encoding the protein can be incorporated into a retroviral, adenoviral or other suitable vector (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

Exemplification

The present invention will now be illustrated by the following Examples, which are not intended to be limiting in any way.

Human Chemokines

The CXC chemokines Mig, IL-8, GROα, NAP-2, GCP-2, ENA78, PF4, the CC chemokines MCP-1, MCP-2, MCP-3, MCP-4, MIP-1α, MIP-1β, RANTES, I309, eotaxin and the chemokine-related lymphotactin were chemically synthesized according to established protocols (Clark-Lewis, I. et al., "Chemical synthesis, purification, and characterization of two inflammatory proteins, neutrophil activating peptide 1 (interleukin-8) and neutrophil activating peptide 2," *Biochemistry* 30: 3128–3135 (1991)). The CXC chemokine IP-10 was purchased from PeproTech, Rocky Hill, N. J.

EXAMPLE 1

Cloning of Receptor cDNA

Standard molecular biology techniques were used (Sambrook, J. et al., 1989, *Molecular Cloning: A Laboratory Manual*, Cold Spring Harbor Laboratory Press, Cold Spring Harbor, N.Y.).

DNA fragments coding for putative T lymphocyte-restricted chemokine receptors were generated using the polymerase chain reaction (PCR). Two degenerate oligonucleotide primers were designed based on conserved motifs of chemokine receptors. Primer design was based on the conserved nucleotide sequences within transmembrane domain 2 (TM2) and transmembrane domain 7 (TM7) of the chemokine receptors IL-8R1, IL-8R2, CC-CKR1, CC-CKR2 and the orphan receptors EBI I, LESTR, and BLR1/MDR15 (EBI I, Birkenbach, M. et al., "Epstein-Barr virus-induced genes: First lymphocyte-specific G protein coupled peptide receptors," *J. Virol.*, 67: 2209–2220 (1993)); LESTR, Loetscher, M. et al., "Cloning of a human seven-transmembrane domain receptor, LESTR, that is highly expressed in leukocytes," *J. Biol. Chem.* 269: 232–237 (1994); and BLR1/MDR15, Dobner, T. et al., "Differentiation-specific expression of a novel G protein-coupled receptor from Burkitt's lymphoma," *Eur. J. Immunol.*, 22: 2795–2799 (1992) and Barella, L. et al., "Sequence variation of a novel heptahelical leucocyte receptor through alternative transcript formation," *Biochem. J.*, 309: 773–779 (1995)).

The sequences of the primers were as follows:
SEQ ID NO:3:
5'-GGG CTG CAG CII T(T/G)(T/G) C(C/A)G AC(A/C) TIC TI(C/T) T-3'
SEQ ID NO:4:
5'-GGG TCT AGA IGG GTT IAI (G/A)CA (G/A)C(T/A) (G/A) (T/C)G-3'

(I=inosine). These primers were used in a polymerase chain reaction (PCR) to amplify DNA fragments using human genomic DNA isolated from human peripheral blood lymphocytes as template as follows. A 100 μl reaction mixture containing 2 μg human genomic DNA, 1× DynaZyme buffer (Finnzymes OY, Espoo, Finland), 1.5 mM MgCl$_2$, 500 μM of each deoxynucleotide, 1 μM of both primers, and 2.5 U of DynaZyme DNA polymerase was subjected to 30 cycles (94° C. for 1 minute; 55° C. for 1 minute; and 72° C. for 2 minutes) on a DNA thermal cycler (Techne PHC-2, Brouwer, Switzerland). PCR products of the predicted size (approximately 700 bp) were cloned into the Gene Scribe-Z vectors pTZ18/19 U/R (USB, Cleveland, Ohio), were partially sequenced (Sanger, F. et al., "DNA sequencing with chain-terminating inhibitors," *Proc. Natl. Acad. Sci. USA*, 74: 5463–5467 (1977)), and were evaluated for their similarity to known chemokine receptors and for expression of their corresponding mRNA in leukocytes. A DNA fragment designated 2MLC22 revealed 64% nucleotide sequence identity with IL-8R2. Fragment 2MLC22 specifically hybridized to RNA from T cells, but not monocytes or neutrophils, as assessed by Northern blot analysis using a hybridization probe prepared by enzymatically labeling 2MLC22 with the radioactive isotope $^{32}$P using Klenow fragment of DNA Polymerase I and a commercially available random-prime labeling kit.

Fragment 2MLC22 was enzymatically labeled with $^{32}$P as described and used as a probe to screen a human tetanus toxoid-specific CD4$^+$ T cell (KT30) cDNA library, prepared in lambda-ZAP Express (Stratagene, Zurich, Switzerland) (Loetscher, M. et al., *J. Biol. Chem.*, 269: 232–237 (1994)). A cDNA library was prepared in a λ ZAP Express system according to the manufacturer's protocol (Stratagene GMBH, Zurich, Switzerland) using poly(A)$^+$ RNA from human tetanus toxoid-specific CD4$^+$ T cells (KT30). The resulting library contained about 1.8×10$^6$ independent clones with an average insert size of approximately 1.1 kb. For plaque hybridization screening, about 4×10$^5$ clones were transferred onto Biodyne nylon membranes (PALL AG, Muttenz, Switzerland) and probed with 2MLC22 which had been labeled to a specific activity of 1×10$^9$ dpm/μg DNA using the high prime DNA labeling kit (Boehringer Mannheim, Mannheim, Germany). Hybridization was carried out in 50% formamide, 6×SSC, 0.5% SDS, 100 μg/ml denatured salmon sperm DNA at 42° C. for 20 hours using 1×10$^6$ dpm 2MLC22/ml hybridization solution. The membranes were washed once in 2×SSC, 0.1% SDS at room temperature for 10 minutes, twice in 1×SSC, 0.1% SDS at 65° C. for 30 minutes, and finally once in 0.5×SSC, 0.1% SDS at 65° C. for 10 minutes. Twenty-three clones were isolated from hybridization positive lambda plaques following the high stringency washes, and the clone with the largest insert (1670 bp) was sequenced. CXCR3 cDNA was subcloned into commercially available plasmid vectors for nucleotide sequencing, generation of hybridization probes, and construction of stably transfected mammalian cell clones expressing CXCR3, and these CXCR3 cDNA-containing constructs are maintained in *E. coli* strains.

Results

A cDNA was isolated from a human CD4$^+$ T cell library by searching for T lymphocyte-specific chemokine receptors (FIG. 1, SEQ ID NO:1). This cDNA was not recovered in the course of searching a commonly used monocyte-derived cDNA library or granulocyte (HL60)-derived cDNA library for novel chemokine receptor cDNAs; however, a direct search of the libraries specifically for CXCR3 cDNA has not been conducted. The CXCR3 cDNA, which was shown to encode an IP-10/Mig receptor (see below), and has an open reading frame (ORF) of 1104 bp beginning at residue 69 which encodes a protein of 368 amino acids with a predicted molecular mass of 40,659 daltons. The amino acid sequence (FIG. 2, SEQ ID NO:2) includes seven putative transmembrane segments, which are characteristic of G-protein et al., "Cloning and chromosomal mapping of three novel genes, GPR9, GPR10, and GPR14 encoding receptors related to interleukin 8, neuropeptide Y, and somatostatin receptors," *Genomics*, 29: 335–344 (1995)).

TABLE 1

Amino Acid Sequence Comparison of IP-10/MigR with Human Chemokine Receptors

|  | IL-8R1 | IL-8R2 | CC-CKR1 | CC-CKR2A | CC-CKR3 | CC-CKR4 | CC-CKR5 | ThromR |
|---|---|---|---|---|---|---|---|---|
| IP10/MigR | 40.9[a] | 40.3 | 34.9 | 34.2 | 34.4 | 35.8 | 36.9 | 27.2 |
| IL-8R1 |  | 77.1 | 33.7 | 32.9 | 34.3 | 39.7 | 34.3 | 29.1 |
| IL-8R2 |  |  | 34.9 | 33.6 | 34.1 | 40.8 | 34.4 | 29.7 |
| CC-CKR1 |  |  |  | 54.1 | 63.1 | 49.3 | 56.3 | 26.8 |
| CC-CKR2A |  |  |  |  | 50.7 | 46.1 | 68.8 | 24.6 |
| CC-CKR3 |  |  |  |  |  | 46.5 | 52.3 | 27.3 |
| CC-CKR4 |  |  |  |  |  |  | 50.0 | 29.2 |
| CC-CKR5 |  |  |  |  |  |  |  | 23.6 |

[a]Numbers refer to percentage amino acid identity. Pairwise protein sequence alignments were carried out using the program PALIGN with an open gap cost and unit gap cost of 3 and 2, respectively.

coupled receptors, and three potential N-glycosylation sites ($Asn^{22}$, $Asn^{32}$, and $Asn^{199}$) (FIG. 2). In addition, one threonine and nine serine residues, which are potential phosphorylation sites for receptor kinases (Palczewski, K. and J. L. Benovic, "G-protein-coupled receptor kinases," *Trends Biochem. Sci.*, 16: 387–391 (1991); Chuang, T. T. et al., "High expression of β-adrenergic receptor kinase in human peripheral blood leukocytes. Isoproterenol and platelet activating factor can induce kinase translocation," *J. Biol. Chem.*, 267: 6886–6892 (1992); and Giannini, E. et al., "Identification of the major phosphorylation sites in human C5a anaphylatoxin receptor in vivo," *J. Biol. Chem.*, 270: 19166–19172 (1995)), can be found in the intracellular COOH-terminal region (FIG. 2).

The 368 amino acid sequence of the receptor (IP-10/MigR, FIG. 2, SEQ ID NO:2) was aligned with the amino acid sequences of other human chemokine receptors, including IL-8R1, IL-8R2, CC-CKR1, CC-CKR2A, CC-CKR3 and CC-CKR4. Multiple protein alignment was performed according to Higgins and Sharp (Higgins, D. G. and P. M. Sharp, "Description of the method used in CLUSTAL," *Gene*, 73: 237–244 (1988)). Double underlined residue in FIG. 2 represent regions of identity between IP-10/MigR and at least two other chemokine receptors. Hyphens indicate gaps in the alignment. The alignment revealed several conserved motifs, particularly in the transmembrane domains and the second intracellular loop. Significant sequence identity with CXC receptors IL-8R1 and IL-8R2, but not with the CC chemokine receptors, was observed in the third and the sixth transmembrane domains (FIG. 2).

The sequence shares 40.9% and 40.3% amino acid identity overall with the IL-8R1 and IL-8R2 receptors, respectively, and 34.2 to 36.9% identity with the five known CC chemokine receptors (Table 1). A lower degree of similarity was found with seven-transmembrane-domain receptors that are expressed in T cells, but which do not bind chemokines, e.g., 27.2% identity with the thrombin receptor (Vu, T.-K. H. et al., "Molecular cloning of a functional thrombin receptor reveals a novel proteolytic mechanism of receptor activation," *Cell*, 64: 1057–1068 (1991)). A truncated clone of unidentified function, with an incomplete coding sequence which can be aligned with that of FIG. 2, was previously isolated from a human genomic DNA library (Marchese, A.

EXAMPLE 2

Biological Activity

Expression in Activated T Lymphocytes

In view of the observed chemokine selectivity, the occurrence of the IP-10/MigR in leukocytes and related cell lines was examined by Northern blot analysis. 10 µg samples of total RNA were examined from freshly isolated human blood monocytes, neutrophils, lymphocytes (PBL), nylon-wool purified T cells, and from cultured cells including cloned human CD4$^+$ T cells (KT30) and CD8$^+$ T cells (ERCD8), cloned NK cells (ERNK57), and PBL cultured for 10 days (1–2.5×10$^6$ cells/ml in RPMI 1640 medium containing 2 mM glutamine, 1× non-essential amino acids, 1 mM sodium pyruvate, 100 µg/ml kanamycin, 5×10$^{-5}$ M 2-mercaptoethanol, and 5% human serum) in the presence of 400 U/ml hrIL-2. (human recombinant IL-2 was a gift of Dr. A. Lanzavecchia, Basel Institute of Immunology, Basel, Switzerland). Agarose gels were stained with ethidium bromide to check the integrity and amount of total RNA on the gel prior to blotting. RNA samples were analyzed with $^{32}$P-labeled 5'-fragment of the IP-10/MigR DNA (10$^9$ cpm/µg DNA) at 5×10$^6$ cpm/ml hybridization solution as described (Loetscher, M. et al., *J. Biol. Chem.*, 269: 232–237 (1994)). The 5'-fragment used as a Northern probe was prepared by digestion of CXCR3 cDNA in pBK-CMV vector (Stratagene GMBH, Zurich, Switzerland) with PstI yielding the 724 bp 5'-end of the CXCR3 cDNA (FIG. 1).

Results

Abundant expression of mRNA of the expected size was found in the cloned CD4$^+$ T cells, KT30, that were used for isolation of the receptor cDNA. Similar levels of expression were observed in the CD8$^+$ T cell clone, ERCD8, and the NK cell clone, ERNK57. In contrast, in freshly isolated blood lymphocytes and nylon-wool purified T cells, IL10/MigR transcripts were barely detectable. However, when these cells were cultured in the presence of IL-2, a strong upregulation was obtained, and the level of receptor mRNA approached that of T and NK cell clones. No IP-10/MigR transcripts were detected under these conditions in freshly isolated blood monocytes, neutrophil leukocytes, or eosinophil leukocytes. Additional leukocyte-related cells that did not express IP-10/MigR mRNA include the mast cell line, HMC-1, the promyelocytic leukemia line, HL60, the histiocytic lymphoma, U937, the chronic myelogenous leukemia line, K562, the acute T cell leukemia line, Jurkat, the acute lymphoblastic leukemia line, Molt, the B-lymphoblastic cell lines Daudi and Raji, lymphocytes from patients with chronic and acute B-lymphoid leukemia (B-CLL and B-ALL), mature basophils from a patient with basophilic leukemia, and the erythroleukemia cell line, HEL. By contrast, the receptors for chemokines which have been shown previously to attract lymphocytes, i.e. MCP-1 MCP-2, MCP-3, MIP-1α, MIP-1β and RANTES (Loetscher, P. et al., "The monocyte chemotactic proteins, MCP-1, MCP-2 and MCP-3, are major attractants for human CD4+ and CD8+ T lymphocytes," FASEB J., 8: 1055–1060 (1994); Carr, M. W. et al, "Monocyte chemoattractant protein 1 acts as a T-lymphocyte chemoattractant. Proc. Natl. Acad. Sci. USA 91: 3652–3656 (1994); Taub, D. D. et al., "Preferential migration of activated CD4+ and CD8+ T cells in response to MIP-1α and MIP-1β," Science, 260: 355–358 (1993); Schall, T. J. et al., "Human macrophage inflammatory protein α (MIP-1α) and MIP-1β chemokines attract distinct populations of lymphocytes," J. Exp. Med., 177: 1821–1825 (1993); Schall, T. J. et al., "Selective attraction of monocytes and T lymphocytes of the memory phenotype by cytokine RANTES," Nature, 347: 669–672 (1990)), are also found in monocytes and granulocytes. The restricted expression of IP-10/MigR in activated T lymphocytes and a natural killer cell line suggests that this novel receptor can mediate selective lymphocyte recruitment.

Stable Transfectants

CXCR3 cDNA was released from pBK-CMV (Stratagene GMBH, Zurich, Switzerland) by digestion with BamHI and XbaI, and was cloned into BamHI and XbaI sites of pcDNA3 (Invitrogen BV, WB Leek, Netherlands) to yield pcDNA3-Clone8, which is maintained and stored Escherichia coli (XL1Blue).

To generate stable transfectants, $4 \times 10^6$ of either mouse pre-B cells (300–19) (Thelen, M. et al., FASEB. J., 2: 2702–2706 (1988)), human promyelocytic cells (GM-1) (Garotta, G. et al., J. Leukocyte Biol., 49: 294–301 (1991)) or human acute T cell leukemia cells (Jurkat) (Loetscher, P. et al., FEBS Lett. 341: 187–192 (1994)), were transfected by electroporation with 20 μg of receptor cDNA in pcDNA3 which was linearized with Bgl II as described previously (Moser, B. et al., Biochem. J., 294: 285–292 (1993)).

IP-10/MigR transfected cells were cloned by limiting dilution under G-418 (Life Technologies, Inc.) selection (1.0 mg/ml G-418 for 300–19 and 0.8 mg/ml G-418 for Jurkat and GM-1 cells). G-418 resistant clones were screened for receptor expression by RNA Dot-blot analysis.

$Ca^{2+}$ Flux

To determine whether the receptor was functional, clones of murine pre-B cells (300–19), human promyelocytic cells (GM-1), and human T cell leukemia cells (Jurkat) were stably transfected with receptor cDNA as described above. Activation of chemokine receptors leads to a transient rise in the cytosolic free $Ca^{2+}$ concentration ($[Ca^{2+}]_i$), and this assay was used to monitor signalling in the transfected cells.

Changes in the cytosolic free $Ca^{2+}$ concentration ($[Ca^{2+}]_i$) were measured in cells loaded with fura-2 by incubation for 30 minutes at 37° C. with 0.1 nmol fura-2 acetoxymethylester per $10^6$ cells in a buffer containing 136 mM NaCl, 4.8 mM KCl, 1 mM $CaCl_2$, 5 mM glucose, and 20 mM HEPES, pH 7.4. After centrifugation, loaded cells were resuspended in the same buffer ($10^6$ cells/ml), stimulated with the indicated chemokine at 37° C., and the $[Ca^{2+}]_i$-related fluorescence changes were recorded (von Tscharner, V. et al., "Ion channels in human neutrophils activated by a rise in free cytosolic calcium concentration," Nature, 324: 69–372 (1986)).

Results

A rapid $[Ca^{2+}]_i$ rise was observed in response to IP-10 and Mig. The chemokine IP-10 has been shown to be expressed in cutaneous delayed-type hypersensitivity reactions (Luster, A. D. et al., "γ-Interferon transcriptionally regulates an early-response gene containing homology to platelet proteins," Nature, 315: 672–676 (1985); Kaplan, G. et al., "The expression of a gamma interferon-induced protein (IP-10) in delayed immune responses in human skin," J. Exp. Med., 166: 1098–1108 (1987)). The chemokine designated Mig was recently identified (Farber, J. M., "A macrophage mRNA selectively induced by gamma-interferon encodes a member of the platelet factor 4 family of cytokines," Proc. Natl. Acad. Sci. USA, 87: 5238–5242 (1990); Farber, J. M., "HuMIG: A new human member of the chemokine family of cytokines," Biochem. Biophys. Res. Commun., 192: 223–230 (1993)). Both chemokines have the CXC arrangement of the first two cysteines like IL-8, but are not chemotactic for neutrophil leukocytes. It was recently reported that IP-10 attracts T lymphocytes (Luster, A. D. and P. Leder, "IP-10 a —C—X—C-chemokine, elicits a potent thymus-dependent antitumor response in vivo," J. Exp. Med., 178: 1057–1065 (1993); Taub, D. D. et al., "Recombinant human interferon-inducible protein 10 is a chemoattractant for human monocytes and T lymphocytes and promotes T cell adhesion to endothelial cells," J. Exp. Med., 177: 1809–1814 (1993)), and that Mig is chemotactic for tumor-associated lymphocytes (Liao, F. et al., "Human mig chemokine: Biochemical and functional characterization," J. Exp. Med., 182: 1301–1314 (1995)).

FIGS. 3A–3C summarize the effects of IP-10 and Mig on cells transfected with the cDNA and expressing the functional IP-10/MigR. As shown by the $[Ca^{2+}]_i$ changes (FIG. 3A), the action of IP-10 and Mig was concentration dependent and already detectable at 1 nM, indicating that both chemokines have high affinity for the novel receptor. The IP-10/MigR transfectants, by contrast, did not respond to any of 16 other potential agonists at concentrations up to 100 nM, including the CXC chemokines IL-8, GROα, NAP-2, GCP-2, ENA78, PF4, the CC chemokines MCP-1, MCP-2, MCP-3, MCP-4, MIP-1α, MIP-1β, RANTES, I309, eotaxin or the chemokine related lymphotactin (not shown). Identical results were obtained with the murine and the human transfected cells. These observations demonstrate that the novel receptor is highly selective for IP-10 and Mig. Accordingly, the receptor is referred to herein as an IP-10/Mig receptor (IP-10/MigR), or as "CXCR3", reflecting its specificity for CXC chemokines.

As shown in FIG. 3B, repeated stimulation with IP-10 or Mig resulted in desensitization typical of chemokine receptors. Furthermore, cross-desensitization occurred when the cells were stimulated with IP-10 followed by Mig or vice versa, confirming that the receptor has high affinity for both chemokines. At 100 nM concentration, it became evident that Mig was more potent in cross-desensitization than IP-10, suggesting higher affinity or binding stability of the IP-10/Mig receptor for Mig.

While expression of functional IP-10/MigR was demonstrated, binding experiments using radioactive ligands revealed non-specific binding between 60 and 80% of the total, preventing determination of binding parameters. Since IP-10 and Mig are highly cationic (pI values of 10.8 and 11.1), nonspecific interaction with cell surface proteoglycans may explain these results. Indeed, chemokine receptorunrelated, heparinase-sensitive binding sites for IP-10 (and PF4) have been detected on a variety of blood and tissue cells (Luster, A. D. et al., "The IP-10 chemokine binds to a specific cell surface heparan sulfate site shared with platelet factor 4 and inhibits endothelial cell proliferation," *J. Exp. Med.,* 182: 219–231 (1995)), and heparan sulfate binds IP-10 and Mig and prevents lymphocyte chemotaxis (not shown). The heparin binding site is probably not involved in CXCR3 receptor binding, and inclusion of a suitable heparin derivative such as chondroitin sulfate in the reaction (e.g., in binding buffer) can be used to inhibit non-specific binding to cells through the heparin binding site.

Chemotaxis

PBL were freshly isolated from donor blood buffy coats. Donor blood buffy coats were provided by the Swiss Central Laboratory Blood Transfusion Service, SRK. Isolation of buffy coat PBL was performed as described in Colotta, F. et al., "Rapid killing actinomycin D-treated tumor cells by human mononuclear cells. I. Effectors belong to the monocyte-macrophage lineage," *J. Immunol.,* 132: 936–944 (1984).

Freshly isolated PBL from donor blood buffy coats were used without further processing, or were used after culturing for 10 days in the presence of IL-2 ($1$–$2.5 \times 10^6$ cells/ml in RPMI 1640 medium containing 2 mM glutamine, 1× nonessential amino acids, 1 mM sodium pyruvate, 100 μg/ml kanamycin, $5 \times 10^{-5}$ M 2-mercaptoethanol, and 5% human serum in the presence of 400 U/ml hrIL-2).

Cell migration was assessed in 48-well chambers (Neuro Probe, Cabin John, Md., USA) using polyvinylpyrrolidone-free polycarbonate membranes (Nucleopore) with 5-μm pores for IP-10/MigR transfected cells (Loetscher, P. et al., *FEBS Lett.* 341: 187–192 (1994)) or with 3-μm pores for human PBL (Loetscher, P. et al., *FASEB J.,* 8: 1055–1060 (1994)). RPMI 1640 supplemented with 20 mM Hepes, pH 7.4, and 1% pasteurized plasma protein solution (Swiss Red Cross Laboratory, Bern, Switzerland) was used to dissolve the chemokines (lower wells), and to dilute the cells (100,000 receptor transfectants or PBL in the upper well). After 60 minutes at 37° C., the membrane was removed, washed on the upper side with PBS, fixed and stained. All assays were done in triplicate, and the migrated cells were counted in five randomly selected fields at 1,000-fold magnification. Spontaneous migration was determined in the absence of chemoattractant.

Results—Transfected Cells

Transfected cells expressing the IP-10/MigR readily migrated toward IP-10 or Mig, while the non-transfected, parental cells did not respond (FIG. 3C). Both agonists showed a typically biphasic concentration dependence. IP-10 induced migration at concentrations above 1 nM, whereas the response of Mig became detectable above 10 nM. The efficacy, which is measured by the maximum number of migrating cells, was about twice as high for Mig as for IP-10. These results demonstrate that the IP-10/MigR, like all known chemokine receptors in leukocytes, mediates chemotaxis in response to ligand.

Results—Human Blood Leukocytes

Figure 4A:
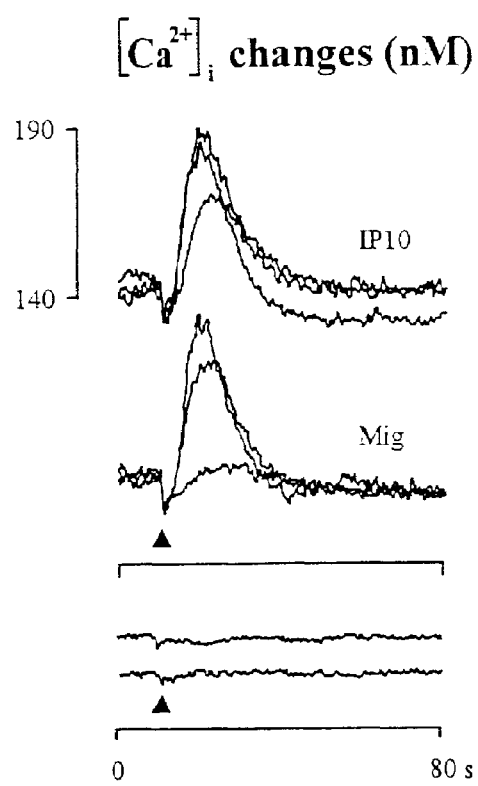
FIGS. 4A–4B are graphs illustrating the responses of peripheral blood lymphocytes (PBL) to IP-10 and Mig. Freshly isolated PBL from donor blood buffy coats were used as such (lower tracings and open symbols), or were used after culturing for 10 days in the presence of IL-2 (400 U/ml) (upper tracings and closed symbols).
Figure 4B:
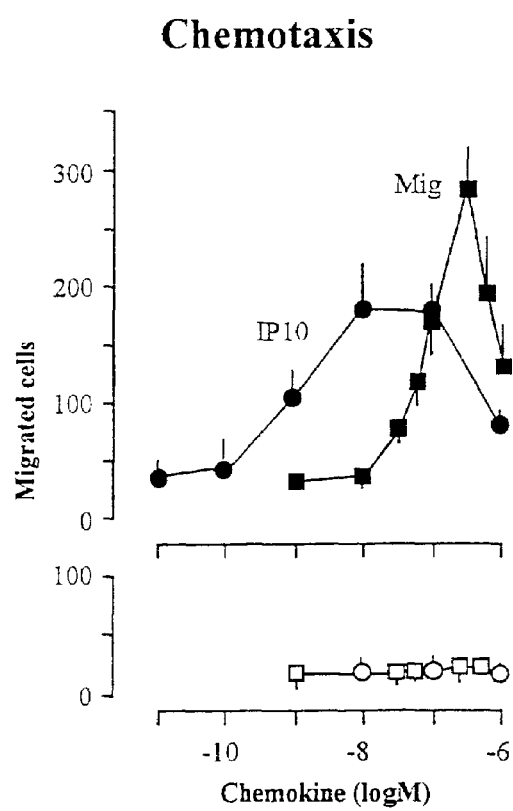

In agreement with the cellular distribution of the IP-10/MigR, activated human T lymphocytes were found to be highly responsive to IP-10 and Mig (FIGS. 4A–4B). The activity of IP-10 and Mig as inducers of $[Ca^{2+}]_i$ changes (FIG. 4A) and in vitro chemotaxis (FIG. 4B) was consistent with the effects observed using transfected cells expressing the IP-10/MigR, with IP-10 being more potent but less efficacious than Mig. Activation of the T lymphocytes by culturing in the presence of IL-2 was required for induction of calcium flux and chemotaxis, and no response was observed with freshly isolated blood lymphocytes under the conditions used.

Equivalents

Those skilled in the art will be able to recognize, or be able to ascertain, using no more than routine experimentation, many equivalents to the specific embodiments of the invention described herein. Such equivalents are intended to be encompassed by the following claims.

---

We claim:

1. A method of detecting or identifying an agent which binds a mammalian CXC Chemokine Receptor 3 (CXCR3) protein or ligand binding variant thereof, comprising combining an agent to be tested and a composition comprising an isolated and/or recombinant mammalian CXCR3 protein or ligand binding variant thereof under conditions suitable for binding of ligand to said mammalian CXCR3 protein or ligand binding variant, and detecting or measuring the formation of a complex between said agent and said mammalian CXCR3 protein or ligand binding variant,
   wherein said mammalian CXCR3 protein or ligand binding variant selectively binds at least one chemokine selected from the group consisting of IP-10 and Mig, and shares at least 90 amino acid sequence identity with SEQ ID NO:2.

2. The method of claim 1, wherein the agent is a ligand selected from the group consisting of human IP-10 and human Mig.

3. The method of claim 2, wherein the ligand is labeled with a label selected from the group consisting of a radioisotope, spin label, antigen label, enzyme label, fluorescent group and chemiluminescent group.

4. The method of claim 1, wherein the assay is a competition assay, in which binding is determined in the presence of one or more ligands selected from the group consisting of human IP-10 and human Mig.

5. A method of detecting or identifying an agent which binds a mammalian CXCR3 protein or a ligand binding variant thereof comprising:
   a) combining an agent to be tested and a host cell expressing recombinant mammalian CXCR3 protein or a ligand binding variant thereof under conditions suitable for binding of ligand to said mammalian CXCR3 protein or ligand binding variant; and
   b) detecting or measuring the formation of a complex between said agent and said mammalian CXCR3 protein or ligand binding variant,
      wherein said mammalian CXCR3 protein or ligand binding variant selectively binds at least one chemokine selected from the group consisting of IP-10 and Mig, and shares at least 90% amino acid sequence identity with SEQ D NO:2.

6. The method of claim 5, wherein the agent is a ligand selected from the group consisting of human IP-10 and human Mig.

7. The method of claim 5, wherein the assay is a competition assay, in which binding is determined in the presence of one or more ligands selected from the group consisting of human IP-10 and human Mig.

8. The method of claim 5, wherein the mammalian CXCR3 protein or ligand binding variant thereof can mediate cellular signalling and/or a cellular response, and the formation of a complex is monitored by detecting or measuring a signalling activity or cellular response induced upon ligand binding to said mammalian CXCR3 protein or ligand binding variant, wherein said signalling activity or cellular response is selected from the group consisting of a transient rise in the concentration of cytosolic free $Ca^{2+}$ ($[Ca^{2+}]_i$), chemotaxis, exocytosis, degranulation and inflammatory mediator release.

9. A method of detecting or identifying an inhibitor of ligand binding to a mammalian CXCR3 protein or a ligand binding variant thereof comprising:
   a) combining an agent to be tested, a ligand of said mammalian CXCR3 protein and a composition comprising isolated and/or recombinant mammalian CXCR3 protein or ligand binding variant thereof under conditions suitable for binding of ligand to said mammalian CXCR3 protein or ligand binding variant; and
   b) detecting or measuring the formation of a complex between said mammalian CXCR3 protein or ligand binding variant and said ligand,
      wherein inhibition of complex formation by the agent is indicative that the agent is an inhibitor, and
      said mammalian CXCR3 protein or ligand binding variant selectively binds at least one chemokine selected from the group consisting of IP-10 and Mig, and shares at least 90% amino acid sequence identity with SEQ ID NO:2.

10. The method of claim 9, wherein the ligand is selected from the group consisting of human IP-10 ad human Mig.

11. The method of claim 9, wherein the composition comprising isolated and/or recombinant mammalian CXCR3 protein or ligand binding variant thereof contains a host cell expressing said recombinant mammalian CXCR3 protein or ligand binding variant thereof.

12. The method of claim 11, wherein said mammalian CXCR3 protein or ligand binding variant thereof can mediate cellular signalling and/or a cellular response, and the formation of a complex is monitored by detecting or measuring a signalling activity or cellular response induced upon ligand binding to said mammalian CXCR3 protein or ligand binding variant, wherein said signalling activity or cellular response is selected from the group consisting of a transient rise in the concentration of cytosolic free $Ca^{2+}$ ($[Ca^{2+}]_i$), chemotaxis, exocytosis, degranulation and inflammatory mediator release.

13. A method of detecting or identifying an inhibitor of ligand binding to a mammalian CXCR3 protein or ligand binding variant thereof comprising:
   a) combining an agent to be tested, a ligand of said mammalian CXCR3 protein and a host cell expressing a recombinant mammalian CXCR3 protein or ligand binding variant thereof under conditions suitable for binding of ligand to said mammalian CXCR3 protein or ligand binding variant; and b) detecting or measuring the formation of a complex between said mammalian CXCR3 protein or ligand binding variant and said ligand, wherein inhibition of complex formation by the agent is indicative that the agent is an inhibitor, and said mammalian CXCR3 protein or ligand binding variant selectively binds at least one chemokine selected from the group consisting of IP-10 and Mig, and shares at least 90% amino acid sequence identity with SEQ ID NO:2.

14. The method of claim 13, wherein the ligand is selected from the group consisting of human IP-10 and human Mig.

15. The method of claim 13, wherein said mammalian CXCR3 protein or ligand binding variant thereof can mediate cellular signalling and/or a cellular response, and the formation of a complex is monitored by detecting or measuring a signaling activity or cellular response induced upon ligand binding to said mammalian CXCR3 protein or ligand binding variant, wherein said signalling activity or cellular response is selected from the group consisting of a transient rise in the concentration of cytosolic free $Ca^{2+}$ ($[Ca^{2+}]_i$), chemotaxis, exocytosis, degranulation and inflammatory mediator release.

16. The method of claim 13 wherein the agent is an antibody or binding fragment thereof.

17. A method of detecting or identifying an inhibitor of a mammalian CXCR3 protein or functional variant thereof comprising combining an agent to be tested, (a) a host cell expressing a recombinant mammalian CXCR3 protein or functional variant thereof, and (b) a ligand or promoter of said mammalian CXCR3 protein or functional variant, under conditions suitable for detecting a ligand- or promoter-induced response, and assessing the ability of the test agent to inhibit said response, wherein inhibition of a ligand- or promoter-induced response by the agent is indicative that the agent is an inhibitor, and said mammalian CXCR3 protein or functional variant selectively binds at least one chemokine selected from the group consisting of IF-10 and Mig, and shares at least 90% amino acid sequence identity with SEQ ID NO:2.

18. The method of claim 17, wherein the response is monitored by detecting or measuring a signaling activity or cellular response of said mammalian CXCR3 protein or functional variant thereof induced upon binding of ligand or promoter, wherein said signalling activity or cellular response is selected from the group consisting of a transient rise in the concentration of cytosolic free $Ca^{2+}$ ($[Ca^{2+}]_i$), chemotaxis, exocytosis, degranulation and inflammatory mediator release.

19. A method of detecting or identifying a promoter of a mammalian CXCR3 protein or functional variant thereof comprising combining an agent to be tested and a host cell expressing a recombinant mammalian CXCR3 protein or functional variant thereof under conditions suitable for detecting a receptor-mediated response, and detecting or measuring said response, wherein induction or stimulation of said response by the agent is indicative that the agent is a promoter, and said mammalian CXCR3 protein or functional variant selectively binds at least one chemokine selected from the group consisting of IP-10 and Mig, and shares at least 90% amino acid sequence identity with SEQ ID NO:2.

20. A method of detecting or identifying an inhibitor of ligand biding to a mammalian CXCR3 protein or a ligand binding variant thereof comprising:

a) combining an agent to be tested, a ligand of said mammalian CXCR3 protein and a composition comprising isolated an/or recombinant mammalian CXCR3 protein or a ligand binding variant thereof under conditions suitable for binding of ligand to said mammalian CXCR3 protein or ligand binding variant; and b) detecting or measuring the formation of a complex between said mammalian CXCR3 protein or ligand binding variant and said ligand, wherein inhibition of complex formation by the agent is indicative that the agent is an inhibitor, and said mammalian CXCR3 protein or ligand binding variant selectively binds at least one chemokine selected from the group consisting of IP-10 and Mig, and is encoded by a nucleic acid sharing at least 90% nucleotide sequence similarity with the coding region of the sequence illustrated in SEQ ID NO:1.

21. A method of detecting or identifying an inhibitor of a mammalian CXCR3 protein or functional variant thereof comprising combining an agent to be tested, (a) a host cell expressing a recombinant mammalian CXCR3 protein or functional variant thereof, and (b) a ligand or promoter of said mammalian CXCR3 protein or functional variant, under conditions suitable for detecting a ligand- or promoter-induced responses, and assessing the ability of the test agent to inhibit said response, wherein inhibition of a ligand- or promoter-induced response by the agent is indicative that the agent is an inhibitor, and said mammalian CXCR3 protein or functional variant selectively binds at least one chemokine selected from the group consisting of IP-10 and Mig, and is encoded by a nucleic acid sharing at least 90% nucleotide sequence similarity with the coding region of the sequence illustrated in SEQ ID NO:1.

22. A method of detecting or identifying a promoter of a mammalian CXCR3 protein or functional variant thereof comprising combining an agent to be tested and a host cell expressing a recombinant mammalian CXCR3 protein or functional variant thereof under conditions suitable for detecting a receptor-mediated response, and detecting or measuring said response, wherein induction or stimulation of said response by the agent is indicative that the agent is a promoter, and said mammalian CXCR3 protein or functional variant selectively binds at least one chemokine selected from the group consisting of IP-10 and Mig, and is encoded by a nucleic acid sharing at least 90% nucleotide sequence similarity with the coding region of the sequence illustrated in SEQ ID NO:1.

23. A method of detecting or identifying an agent which binds a mammalian CXCR3 protein or ligand binding variant thereof of claim 1, wherein the mammalian CXCR3 protein or ligand binding variant thereof is a human CXCR3 or ligand binding variant thereof.

24. A method of detecting or identifying an agent which binds a mammalian CXCR3 protein or a ligand binding variant thereof of claim 5, wherein the mammalian CXCR3 protein or ligand binding variant thereof is a human CXCR3 or ligand binding variant thereof.

25. A method of detecting or identifying an inhibitor of ligand binding to a mammalian CXCR3 protein or a ligand binding variant thereof of claim 9, wherein the mammalian CXCR3 protein or ligand binding variant thereof is a human CXCR3 or ligand binding variant thereof.

26. A method of detecting or identifying an inhibitor of ligand binding to a mammalian CXCR3 protein or ligand binding variant thereof of claim 13, wherein the mammalian CXCR3 protein or ligand binding variant thereof is a human CXCR3 or ligand binding variant thereof.

27. A method of detecting or identifying an inhibitor of a mammalian CXCR3 protein or functional variant thereof of claim 17, wherein the mammalian CXCR3 protein or functional variant thereof is a human CXCR3 or functional variant thereof.

28. A method of detecting or identifying a promoter of a mammalian CXCR3 protein of functional variant thereof of claim 19, wherein the mammalian CXCR3 protein or functional variant thereof is a human CXCR3 or functional variant thereof.

29. A method of detecting or identifying an inhibitor of ligand binding to a human CXCR3 protein comprising:
   a) combining an agent to be tested, a ligand of said CXCR3 protein and a composition comprising recombinant human CXCR3 protein under conditions suitable for binding of ligand to said human CXCR3 protein; and
   b) detecting or measuring the formation of a complex between said human CXCR3 protein and said ligand,
   wherein inhibition of complex formation by the agent is indicative that the agent is an inhibitor, and
   said human CXCR3 protein selectively binds at least one chemokine selected from the group consisting of human IP-10 or human Mig and comprises the extracellular N-terminal segment of the protein shown in FIG. 2 (SEQ ID NO:2).

30. The method of claim 29, wherein the ligand is human IP-10 or human Mig.

31. The method of claim 29, wherein the ligand is labeled with a label selected from the group consisting of a radioisotope, spin label, antigen label, enzyme label, fluorescent group and chemiluminescent group.

32. The method of claim 29, wherein the composition comprising recombinant human CXCR3 protein comprises a membrane fraction of host cells expressing recombinant human CXCR3 protein.

33. The method of claim 32, wherein the ligand is human IP-10 or human Mig.

34. The method of claim 33, wherein the ligand is labeled with a label selected from the group consisting of a radioisotope, spin label, antigen label, enzyme label, fluorescent group and chemiluminescent group.

35. A method of detecting or identifying an inhibitor of ligand binding to a human CXCR3 protein comprising:
   a) combining an agent to be tested, a ligand of said human CXCR3 protein and a host cell expressing a recombinant human CXCR3 protein under conditions suitable for binding of ligand to said human CXCR3 protein; and
   b) detecting or measuring the formation of a complex between said protein and said ligand,
      wherein inhibition of complex formation by the agent is indicative that the agent is an inhibitor, and
      said human CXCR3 protein selectively binds at least one chemokine selected from the group consisting of human IP-10 or human Mig and comprises the extracellular N-terminal segment of the protein shown in FIG. 2 (SEQ ID NO:2).

36. The method of claim 35, wherein the ligand is human IP-10 or human Mig.

37. The method of claim 35, we the ligand is labeled with a label selected from the group consisting of a radioisotope, spin label, antigen label, enzyme label fluorescent group and chemiluminescent group.

38. The method of claim 35, wherein the human CXCR3 protein can mediate cellular signaling and/or a cellular response, and the formation of a complex is monitored by detecting or measuring a signaling activity or cellular response of said CXCR3 protein induced upon ligand binding, wherein said signalling activity or cellular response is selected from the group consisting of a transient rise in the concentration of cytosolic free $Ca^{2+}$ ($[Ca^{2+}]_i$), chemotaxis, exocytosis, degranulation and inflammatory mediator release.

39. A method of detecting or identifying an agent which binds a mammalian CXCR3 protein or ligand binding variant thereof, comprising combining an agent to be tested and a composition comprising an isolated and/or recombinant mammalian CXCR3 protein or ligand big variant thereof under conditions suitable for binding of ligand to said ian CXCR3 protein or ligand binding variant, and detecting or measuring the formation of a complex between said agent and said mammalian CXCR3 protein or ligand binding variant,
   wherein said mammalian CXCR3 protein or ligand binding variant selectively binds at least one chemokine selected from the group consisting of IP-10 and Mig, and is encoded by a nucleic acid that hybridizes, under high stringency wash conditions of 2×SSC, 0.1% SDS at room temperature for ten minutes followed by two washes in 1×SSC, 0.1% SDS at 65° C. for thirty minutes and a final wash in 0.5×SSC, 0.1% SDS at 65° C. for ten minutes, to a nucleic acid selected from the group consisting of:
      a) the complement of SEQ ID NO:1; and
      b) the complement of a portion of SEQ ID NO:1 comprising the open reading frame.

40. A method of detecting or identifying an agent which binds a mammalian CXCR3 protein or ligand binding variant thereof of claim 39, wherein the mammalian CXCR3 protein or ligand binding variant thereof is a human CXCR3 or ligand binding variant thereof.

41. A method of detecting or identifying an inhibitor of ligand binding to a mammalian CXCR3 protein or a ligand binding variant thereof comprising:
   a) combining an agent to be tested, a ligand of said mammalian CXCR3 protein and a composition comprising isolated and/or recombinant an CXCR3 protein or a ligand binding variant thereof under conditions suitable for binding of ligand to said mammalian CXCR3 protein or ligand binding variant; and
   b) detecting or measuring the formation of a complex between said mammalian CXCR3 protein or ligand binding variant and said ligand,
      wherein inhibition of complex formation by the agent is indicative that the agent is an inhibitor, and
      said ma mammalian CXCR3 protein or ligand binding variant selectively binds at least one chemokine selected from the group consisting of IP-10 and Mig, and is encoded by a nucleic acid that hybridizes, under high stringency wash conditions of 2×SSC, 0.1% SOS at room temperature for ten minutes followed by two washes in 1×SSC, 0.1% SDS at 65° C. for thirty minutes and a final wash in 0.5×SSC, 0.1% SDS at 65° C. for ten minutes, to a nucleic acid selected from the group consisting of:

i) the complement of SEQ ID NO:1; and
ii) the complement of a portion of SEQ ID NO:1 comprising the open reading frame.

42. A method of detecting or identifying an inhibitor of ligand binding to a mammalian CXCR3 protein or a ligand binding variant thereof of claim 41, wherein the mammalian CXCR3 protein or ligand binding variant thereof is a human CXCR3 or ligand binding variant thereof.

43. A method of detecting or identifying an inhibitor of a mammalian CXCR3 protein or functional variant thereof comprising combining an agent to be tested,
   (a) a host cell expressing a recombinant mammalian CXCR3 protein or functional variant thereof, and
   (b) a ligand or promoter of said mammalian CXCR3 protein, under conditions suitable for detecting a ligand- or promoter-induced response, and assessing the ability of the test agent to inhibit said response,
       wherein inhibition of a ligand- or promoter-induced response by the agent is indicative that the agent is an inhibitor, and
       said mammalian CXCR3 protein or functional variant selectively binds at least one chemokine selected from the group consisting of IP-10 and Mig, and is encoded by a nucleic acid that hybridizes, under high stringency wash conditions of 2×SSC, 0.1% SDS at room temperature for ten minutes followed by two washes in 1×SSC, 0.1% SDS at 65° C. for thirty minutes and a final wash in 0.5×SSC, 0.1% SDS at 65° C. for ten minutes, to a nucleic acid selected from the group consisting of:
   i) the complement of SEQ D NO:1; and
   ii) the complement of a portion of SEQ ID NO:1 comprising the open reading frame.

44. A method of detecting or identifying an inhibitor of a mammalian CXCR3 protein or functional variant thereof of claim 43, wherein the mammalian CXCR3 protein or functional variant thereof is a human CXCR3 or functional variant thereof.

45. A method of detecting or identifying a promoter of a mammalian CXCR3 protein or functional variant thereof comprising combining an agent to be tested and a host cell expressing a recombinant mammalian CXCR3 protein or functional variant thereof under conditions suitable for detecting a receptor-mediated response, and detecting or measuring said response,
   wherein induction or stimulation of said response by the agent is indicative that the agent is a promoter, and
   said mammalian CXCR3 protein or functional variant selectively binds at least one chemokine selected from the group consisting of IP-10 and Mig, and is encoded by a nucleic acid that hybridizes, under high stringency wash conditions of 2×SSC, 0.1% SDS at room temperature for ten minutes followed by two washes in 1×SSC, 0.1% SDS at 65° C. for thirty minutes and a final wash in 0.5×SSC, 0.1% SDS at 65° C. for ten minutes, to a nucleic acid selected from the group consisting of:
   i) the complement of SEQ ID NO:1; and
   ii) the complement of a portion of SEQ ID NO:1 comprising the open reading frame.

46. A method of detecting or identifying a promoter of a mammalian CXCR3 protein or functional variant thereof of claim 45, wherein the mammalian CXCR3 protein or functional variant thereof is a human CXCR3 or functional variant thereof.

47. The method of claim 1 wherein said mammalian CXCR3 protein or ligand binding variant comprises the extracellular N-terminal segment of the protein sown in FIG. 2 (SEQ ID NO:2).

48. The method of claim 5 wherein said mammalian CXCR3 protein or ligand binding variant comprises the extracellular N-terminal segment of the protein shown in FIG. 2 (SEQ ID NO:2).

49. The method of claim 9 wherein said mammalian CXCR3 protein or ligand binding variant comprises the extracellular N-terminal segment of the protein shown in FIG. 2 (SEQ ID NO:2).

50. The method of claim 13 wherein said mammalian CXCR3 protein or ligand binding variant comprises the extracellular N-terminal segment of the protein shown in FIG. 2 (SEQ ID NO:2).

51. The method of claim 17 wherein said mammalian CXCR3 protein or functional variant comprises the extracellular N-terminal segment of the protein shown in FIG. 2 (SEQ ID NO:2).

52. The method of claim 19 wherein said mammalian CXCR3 protein or functional variant comprises the extracellular N-terminal segment of the protein shown in FIG. 2 (SEQ ID NO:2).

53. The method of claim 20 wherein said mammalian CXCR3 protein or ligand binding variant comprises the extracellular N-terminal segment of the protein shown in FIG. 2 (SEQ ID NO:2).

54. The method of claim 21 wherein said mammalian CXCR3 protein or functional variant comprises the extracellular N-terminal segment of the protein shown in FIG. 2 (SEQ ID NO: 2).

55. The method of claim 22 wherein said mammalian CXCR3 protein or functional variant comprises the extracellular N-terminal segment of the protein shown in FIG. 2 (SEQ ID NO:2).

56. The method of claim 39 wherein said mammalian CXCR3 protein or ligand binding variant comprises the extracellular N-terminal segment of the protein shown in FIG. 2 (SEQ ID NO:2).

57. The method of claim 41 wherein said mammalian CXCR3 protein or ligand binding variant comprises the extracellular N-terminal segment of the protein shown in FIG. 2 (SEQ ID NO:2).

58. The method of claim 43 wherein said mammalian CXCR3 protein or functional variant comprises the extracellular N-terminal segment of the protein shown in FIG. 2 (SEQ ID NO:2).

59. The method of claim 45 wherein said mammalian CXCR3 protein or functional variant comprises the extracellular N-terminal segment of the protein shown in FIG. 2 (SEQ ID NO:2).

60. The method of claim 19 wherein said receptor-mediated response is selected from the group consisting of a transient rise in the concentration of cytosolic free $Ca^{2+}$ ($[Ca^{2+}]_i$), chemotaxis, exocytosis, degranulation and inflammatory mediator release.

61. The method of claim 22 wherein said receptor-mediated response is selected from the group consisting of a transient rise in the concentration of cytosolic free $Ca^{2+}$ ($[Ca^{2+}]_i$), chemotaxis, exocytosis, degranulation and inflammatory mediator release.

62. The method of claim 45 wherein said receptor-mediated response is selected from the group consisting of a transient rise in the concentration of cytosolic free $Ca^{2+}$ ($[Ca^{2+}]_i$), chemotaxis, exocytosis, degranulation and inflammatory mediator release.

* * * * *

UNITED STATES PATENT AND TRADEMARK OFFICE
CERTIFICATE OF CORRECTION

PATENT NO. : 7,029,862 B1
APPLICATION NO. : 09/633541
DATED : April 18, 2006
INVENTOR(S) : Marcel Loetscher and Bernhard Moser It is certified that error appears in the above-identified patent and that said Letters Patent is hereby corrected as shown below:

Column 45
    In Claim 1, column 45, line 27, "90 amino acid" should be --90% amino acid--;

In Claim 5, column 45, line 55, "SEQ D" should be --SEQ ID--,

Column 46
    In Claim 10, column 46, line 41, "ad" should be --and--,

Column 47
    In Claim 15, column 47, line 17, "signaling" should be --signalling--, In Claim 17, column 47, line 41, "IF-10" should be --IP-10--, In Claim 18, column 47, line 45, "signaling" should be --signalling--, Column 48
    In Claim 20, column 48, line 2, "biding" should be --binding--, In Claim 20, column 48, line 6, "an/or" should be --and/or--, Column 50
    In Claim 37, column 50, line 1, "we" should be --wherein--, In Claim 39, column 50, line 19, "big" should be --binding--

In Claim 39, column 50, line 20, "ian" should be --mammalian--

In Claim 41, column 50, line 58, "ma" should be deleted,

In Claim 41, column 50, line 63, "SOS" should be --SDS--

Column 51
    In Claim 43, column 51, line 31, "SEQ D" should be --SEQ ID--,

Column 52
    In Claim 47, column 52, line 3, "sown" should be --shown--.

UNITED STATES PATENT AND TRADEMARK OFFICE
CERTIFICATE OF CORRECTION

PATENT NO. : 7,029,862 B1
APPLICATION NO. : 09/633541
DATED : April 18, 2006
INVENTOR(S) : Marcel Loetscher and Bernhard Moser It is certified that error appears in the above-identified patent and that said Letters Patent is hereby corrected as shown below:

Column 52
In Claim 47, column 52, line 3, "sown" should be --shown--.

Signed and Sealed this

Fifteenth Day of August, 2006

JON W. DUDAS
*Director of the United States Patent and Trademark Office*